US007939064B2

(12) United States Patent
Jeyaseelan et al.

(10) Patent No.: US 7,939,064 B2
(45) Date of Patent: May 10, 2011

(54) PHOSPHOLIPASE(S) AND USE(S) THEREOF

(75) Inventors: Kandiah Jeyaseelan, Singapore (SG); Dyi Ni Charmian Cher, Singapore (SG); Arunmozhiarasi Armugam, Singapore (SG)

(73) Assignee: National University of Singapore, Singapore (SG)

( * ) Notice: Subject to any disclaimer, the term of this patent is extended or adjusted under 35 U.S.C. 154(b) by 318 days.

(21) Appl. No.: 12/087,989

(22) PCT Filed: Jul. 16, 2006

(86) PCT No.: PCT/SG2006/000162
§ 371 (c)(1),
(2), (4) Date: Jul. 18, 2008

(87) PCT Pub. No.: WO2006/135345
PCT Pub. Date: Dec. 21, 2006

(65) Prior Publication Data
US 2009/0252718 A1    Oct. 8, 2009

(51) Int. Cl.
*A61K 38/43*      (2006.01)
*A61K 38/00*      (2006.01)
*C12N 9/20*       (2006.01)
*C12N 9/00*       (2006.01)
*C07H 21/02*      (2006.01)

(52) U.S. Cl. ...... 424/94.1; 424/94.6; 435/198; 435/183; 536/23.1

(58) Field of Classification Search ............... 424/94.1, 424/94.6; 435/198, 183; 536/23.1
See application file for complete search history.

(56) References Cited

OTHER PUBLICATIONS

Armugam et al., A secretory phospholipase A2-mediated neuroprotection and anti-apoptosis. BMC Neuroscience, 2009, vol. 10:1-13.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
S.T. Ohnishi, "A Prostaglandin Oligomeric Derivative Inhibits Activities of Phospholipase and Protease: A Possible Mechanism of Membrane Protection during Ischemia," *Cell Biochemistry and Function*, vol. 7, pp. 51-55 (1989).
C.D.M. Cher et. al., "Pulmonary Inflammation and Edema Induced by Phospholipase $A_2$," *The Journal of Biological Chemistry*, vol. 278, No. 33, pp. 31352-31360 (2003).
G.Y. Sun et. al., "Phospholipase $A_2$ in the Central Nervous System: Implications for Neurodegenerative Diseases," *Journal of Lipid Research*, vol. 45, pp. 205-213 (2004).
R. Lachumanan et al., "In Situ Hybridization and Immunohistochemical Analysis of the Expression of Cardiotoxin and Neurtoxin Genes in *Naja Naja sputatrix*," *The Journal of Histochemistry and Cytochemistry*, vol. 47, No. 4, pp. 551-560 (1999).
Argraves W.S., et.al., "Fibulins: Physiological and Disease Perspectives", EMBO reports, 2003, vol. 4 (12):1127-1131.
Armugam A., et.al., "Cloning and Characterization of cDNAs Encoding Three Isoforms of Phospholipase $A_2$ in Malayan Spitting Cobra (*Naja Naja Sputatrix*) Venom", Toxicon, 1997, vol. 35(1):27-37.
Baker-LePain J.C., et.al., "Glucose-Regulated Protein 94/Glycoprotein 96 Elicits Bystander Activation of CD4[+] T Cell Th1 Cytokine Production In Vivo", The Journal of Immunology, 2004, vol. 172:4195-4203.
Barone F.C., et.al., "Tumor Necrosis Factor-α, A Mediator of Focal Ischemic Brain Injury", Stroke, 1997, vol. 28(6):1233-1244.
Bertorelli R., et.al., "MK 801 and Dexamethasone Reduce Both Tumor Necrosis Factor Levels and Infarct Volume After Focal Cerebral Ischemia in the Rat Brain", Neuroscience Letters, 1998, vol. 246:41-44.
Beschorner R., et.al., "Differential Regulation of the Monocytic Calcium-Binding Peptides Macrophage-Inhibiting Factor Related Protein-8 (MRP8/S100A8) and Allograft Inflammatory Factor-1 (AIF-1) Following Human Traumatic Brain Injury", Acta Neuropathol, 2000, vol. 100:627-634.
Blake G.J. and Ridker P.M., "Novel Clinical Markers of Vascular Wall Inflammation", Circulation Research, 2001, vol. 89:763-771.
Bonventre J.V., et.al., "Reduced Fertility and Postischaemic Brain Injury in Mice Deficient in Cytosolic Phospholipase $A_2$", Nature, 1997; vol. 390:622-625.
Buchan A.M., et.al., "The Effect of the NMDA Receptor Antagonist MK-801 on Cerebral Blood Flow and Infarct Volume in Experimental Focal Stroke", Brain Research, 1992, vol. 574:171-177.

(Continued)

*Primary Examiner* — Ganapathirama Raghu
(74) *Attorney, Agent, or Firm* — Dickstein Shapiro LLP

(57) ABSTRACT

The invention relates to phospholipase(s), isoforms, derivatives, mutants and/or fragments thereof, for the preparation of a medicament for the treatment and/or prevention of ischemia. Preferred is the use of secretory phospholipase, particularly phospholipase $A_2$, and even more particularly phospholipase $A_2$ derived from the snake venom of *Naja sputatrix*.

16 Claims, 21 Drawing Sheets

OTHER PUBLICATIONS

Figure 1A:
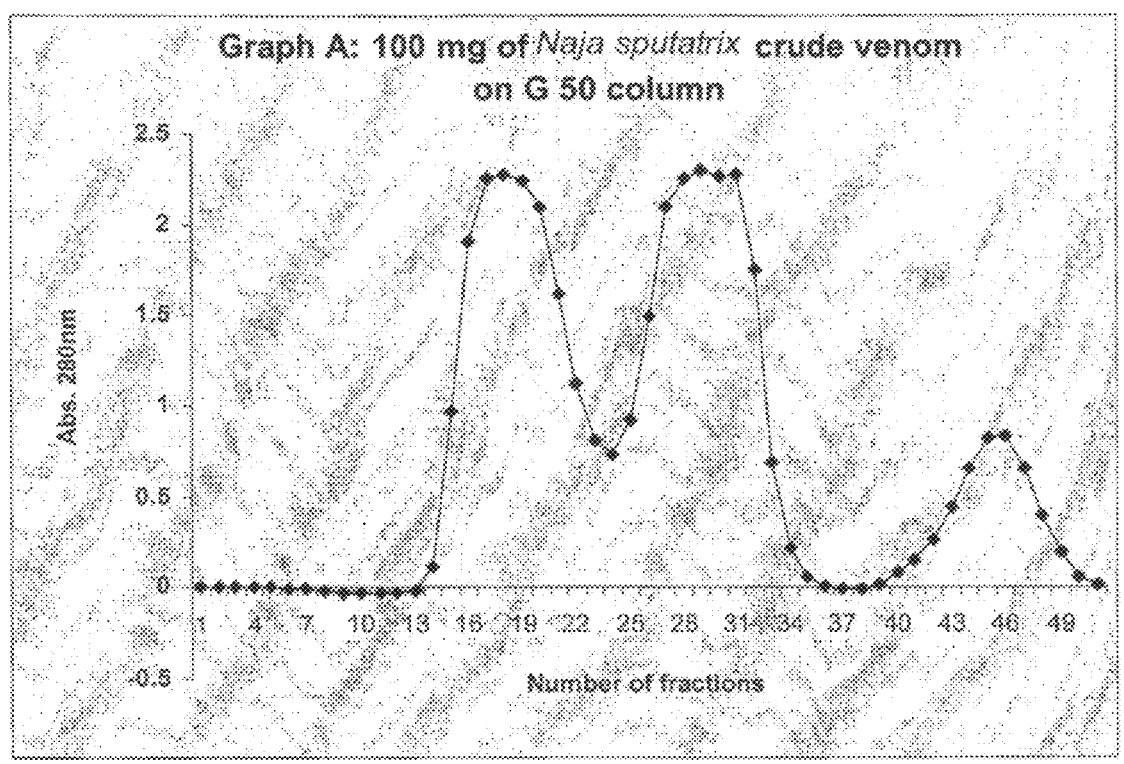

Chen Z-L. and Strickland S., "Neuronal Death in the Hippocampus is Promoted by Plasmin-Catalyzed Degradation of Laminin", Cell, 1997, vol. 91:917-925.

Choi D., "Stroke", Neurobiology of Disease, 2000 vol. 7:552-558.

del Zoppo G.J., et.al., "Polymorphonuclear Leukocytes Occlude Capillaries Following Middle Cerebral Artery Occlusion and Reperfusion in Baboons", Stroke, 1991, vol. 22(10):1276-1283.

Dirnagl U., et.al., "Pathobiology of Ischaemic Stroke: An Integrated View", Trends in Neurosciences, 1999, vol. 22(9):391-397.

Ellison J.A., et.al., "Osteopontin and its Integrin Receptor $\alpha V \beta 3$ Are Upregulated During Formation of the Glial Scar After Focal Stroke", Stroke, 1998, vol. 29:1698-1707.

Fisher M., "The Ischemic Penumbra: Identification, Evolution and Treatment Concepts", Cerebrovascular Diseases, 2004, vol. 17(suppl 1):1-6.

Fisher M. and Schaebitz W., "An Overview of Acute Stroke Therapy", Archives of Internal Medicine, 2000, vol. 160:3196-3206.

Fujimura M., et.al., "Early Appearance of Activated Matrix Metalloproteinase-9 and Blood-Brain Barrier Disruption in Mice After Focal Cerebral Ischemia and Reperfusion", Brain Research, 1999, vol. 842:92-100.

Furlan A., et.al., "Intra-arterial Prourokinase for Acute Ischemic Stroke: The PROACT II Study: A Randomized Controlled Trial", JAMA, 1999, vol. 282(21):2003-2011.

Furukawa K., et.al., "The Actin-Severing Protein Gelsolin Modulates Calcium Channel and NMDA Receptor Activities and Vulnerability of Excitotoxicity in Hippocampal Neurons", The Journal of Neuroscience, 1997, vol. 17(21):8178-8186.

Hakim A.M., "The Cerebral Ischemic Penumbra", The Canadian Journal of Neurological Sciences, 1987, vol. 14:557-559.

Hamann G.F., et.al., "Microvascular Basal Lamina Antigens Disappear During Cerebral Ischemia and Reperfusion", Stroke, 1995, vol. 26:2120-2126.

Hsu C.Y., et.al., "Expression of Immediate Early Gene and Growth Factor mRNAs in a Focal Cerebral Ischemia Model in the Rat", Stroke, 1993, vol. 24(12)[suppl I]:I78-I81.

Hunter A.J., et.al., "Animal Models of Acute Ischaemic Stroke: Can They Predict Clinically Successful Neuroprotective Drugs?", Trends in Pharmacological Sciences, 1995, vol. 16:123-128.

Iadecola C., "Bright and Dark Sides of Nitric Oxide in Ischemic Brain Injury", Trends in Neurosciences, 1997, vol. 20(3):132-139.

Izeboud C.A., et.al. "Endotoxin-Induced Liver Damage in Rats is Minimized by $\beta 2$-Adreno-Ceptor Stimulation", Inflammation Research, 2004, vol. 53:93-99.

Jeyaseelan K., et.al., "Structure and Phylogeny of the Venom Group I Phospholipase $A_2$ Gene", Molecular Biology and Evolution, 2000, vol. 17(7):1010-1021.

Karpiak S.E., et.al., "Animal Models for the Study of Drugs in Ischemic Stroke", Annual Review of Pharmacology and Toxicology, 1989, vol. 29:403.

Kilic E., et.al., "Effects of Recombinant Tissue Plasminogen Activator After Intraluminal Thread Occlusion in Mice: Role of Hemodynamic Alterations", Stroke, 2001, vol. 32:2641.

Kini R.M., "Phospholipase $A_2$—A Complex Multifunctional Protein Puzzle", Venom Phospholipase $A_2$ Enzymes: Structure, Function and Mechanism, 1997, pp. 1.

Kinouchi H., et.al., "Attenuation of focal cerebral ischemic injury in transgenic mice overexpressing CuZn superoxide dismutase", Proceedings of the National Academy of Sciences USA, 1991, vol. 88:11158.

Kondo T., et.al., "Reduction of CuZn-Superoxide Dismutase Activity Exacerbates Neuronal Cell Injury and Edema Formation after Transient Focal Cerebral Ischemia", The Journal of Neuroscience, 1997, vol. 17(11):4180-4189.

Li J., et.al., "Macrophage-Dependent Regulation of Syndecan Gene Expression", Circulation Research, 1997, vol. 81:785-796.

Liu T., "Tumor Necrosis Factor-$\alpha$ Expression in Ischemic Neurons", Stroke, 1994, vol. 25(7):1481-1488.

MacManus J.P., et.al., "Translation-State Analysis of Gene Expression in Mouse Brain After Focal Ischemia", Journal of Cerebral Blood Flow & Metabolism, 2004, vol. 24(6):657-667.

Matsui T., et.al., "Astrocytic Activation and Delayed Infarct Expansion After Permanent Focal Ischemia in Rats. Part I: Enhanced Astrocytic Synthesis of S-100$\beta$ in the Periinfarct Area Precedes Delayed Infarct Expansion", Journal of Cerebral Blood Flow & Metabolism, 2002, vol. 22(6):711-722.

McKay S., et.al., "Pro-Inflammatory Cytokines Induce c-fos Expression Followed by IL-6 Release in Human Airway Smooth Muscle Cells", Mediators of Inflammation, 2001, vol. 10:135-142.

Nagahiro S., et.al., "Pathophysiology and Treatment of Cerebral Ischemia", The Journal of Medical Investigation, 1998, vol. 45:57-70.

Nagai N., et.al., "Tissue-type Plasminogen Activator Is Involved in the Process of Neuronal Death Induced by Oxygen-Glucose Deprivation in Culture", Journal of Cerebral Blood Flow and Metabolism, 2001, vol. 21(6):631-634.

Paglini G., et.al., "Suppresion of Radixin and Moesin alters Growth Cone Morphology, Motility, and Process Formation in Primary Cultured Neurons", The Journal of Cell Biology, 1998, vol. 143(2):443-445.

Pisani A., et.al., "Calcium Signaling and Neuronal Vulnerability to Ischemia in the Striatum", Cell Calcium, 2004, vol. 36:277-284.

Read S.J., et.al., "Stroke Genomics: Approaches to Identify, Validate, and Understand Ischemic Stroke Gene Expression", Journal of Cerebral Blood Flow and Metabolism, 2001, vol. 21(7):755-758.

Rosenberg G.A., "Matrix Metalloproteinases in Brain Injury", Journal of Neurotrauma, 1995, vol. 12(5):833-842.

Rosenberg G.A., et.al. "Proteolytic Cascade Enzymes Increase in Focal Cerebral Ischemia in Rat", Journal of Cerebral Blood Flow & Metabolism, 1996, vol. 16:360-366.

Rothwell N.J. and Hopkins S.J., "Cytokines and the Nervous System II: Actions and Mechanisms of Action", Trends in Neurosciences, 1995, vol. 18(3):130-136.

Schaller B. and Graf R., "Cerebral Ischemia and Reperfusion: The Pathophysiologic Concept as a Basis for Clinical Therapy", Journal of Cerebral Blood Flow & Metabolism, 2004, vol. 24(4):351-371.

Sherman D.G., et.al., "Intravenous Ancrod for Treatment of Acute Ischemic Stroke: The STAT Study: A Randomized Controlled Trial", JAMA, 2000, vol. 283(18):2395-2403.

Sim F.J., et.al., "Expression of the POU-Domain Transcription Factors SCIP/Oct-6 and Brn-2 is associated with Schwann Cell but Not Oligodendrocyte Remyelination of the CNS", Molecular and Cellular Neuroscience, 2002, vol. 20:669-682.

Smith W.S., "Pathophysiology of Focal Cerebral Ischemia: a Therapeutic Perspective", J. Vasc. Interv. Radiol, 2004, vol. 15:S3-S12.

Tan N-H and Arunmozhiarasi A., "The Anticoagulant Activity of Malayan Cobra (*Naja Naja Sputatrix*) Venom and Venom Phospholipase $A_2$ Enzymes", Biochemistry International, 1989, vol. 19(4):803-810.

Tsirka S.E., et.al., "An Extracellular Proteolytic Cascade Promotes Neuronal Degeneration in the Mouse Hippocampus", The Journal of Neuroscience, 1997, vol. 17(2):543-552.

Uemura Y., et.al., "Focal Ischemia in Rats Causes Time-Dependent Expression of c-fos Protein Immunoreactivity in Widespread Regions of Ipsilateral Cortex", Brain Research, 1991, vol. 552:99-105.

Valentin E. and Lambeau G., "Increasing Molecular Diversity of Secreted Phospholipases $A_2$ and Their Receptors and Binding Proteins", Biochimica et Biophysica Acta, 2000, vol. 1488:59-70.

Walther T., et al.,"Ischemic Injury in Experimental Stroke Depends on Angiotensin II", The FASEB Journal, 2002, vol. 16:169-176.

Wang H., et.al., "Use of Suppresion Subtractive Hybridization for Differential Gene Expression in Stroke: Discovery of CD44 Gene Expression and Localization in Permanent Focal Stroke in Rats", Stroke, 2001, vol. 32:1020-1027.

Wang X., et.al., "Delayed Expression of Osteopontin after Focal Stroke in the Rat", The Journal of Neuroscience, 1998, vol. 18(6):2075-2083.

Wang X., et.al., "CD44 Deficiency in Mice Protects Brain From Cerebral Ischemia Injury", Journal of Neurochemistry, 2002, vol. 83:1172-1179.

Wang X., et.al., "Monocyte Chemoattractant Protein—1 Messenger RNA Expression in Rat Ischemic Cortex", Stroke, 1995, vol. 26(4):661-666.

Wang X., et.al., "Expression of Interleukin-6, *c-fos*, and zif268 mRNAs in Rat Ischemic Cortex", Journal of Cerebral Blood Flow and Metabolism, 1995, vol. 15:166-171.

Warlow C., et.al., In Stroke: Practical Guide to Management. Chapter 6: "What Caused This Transient or Persisting Ischaemic Event?", Oxford: Blackwell Science, 2001, pp. 223-230.

Warlow C., et.al., "Stroke", The Lancet, 2003, vol. 362:1211-1224.

Weisbrot-Lefkowitz M., et.al., "Overexpression of Human Glutathione Peroxidase Protects Transgenic Mice Against Focal Cerebral Ischemia/Reperfusion Damage", Molecular Brain Research, 1998, vol. 53:333-338.

Yang G., et.al., "Reduction of Vasogenic Edema and Infarction by MK-801 in Rats after Temporary Focal Cerebral Ischemia", Neurosurgery, 1994, vol. 34(2):339-345.

Ye Z-R., et.al., "Mechanisms of Neuronal Cell Death after Ischemic Injury to the Brain", Current Review of Cerebrovascular Disease, pp.15-24.

Zhao Q., et.al., "Delayed Treatment With the Spin Trap α-Phenyl-N-Tert-Butyl Nitrone (PBN) Reduces Infarct Size Following Transient Middle Cerebral Artery Occlusion in Rats", Acta Physiol. Scand., 1994, vol. 152:349-350.

Zivin J.A., et.al., "Tissue Plasminogen Activator Reduces Neurological Damage After Cerebral Embolism", Science, 1985, vol. 230(4731):1289-1292.

Zivin J.A., et.al., "Tissue Plasminogen Activator: Reduction of Neurologic Damage After Experimental Embolic Stroke", Archives of Neurology, 1988, vol. 45:387-391.

Six et al., "The expanding superfamily of phospholipase $A_2$ enzymes: classification and characterization," *Biochimica et Biophysica Acta*, 1488 (2000) 1-19.

\* cited by examiner

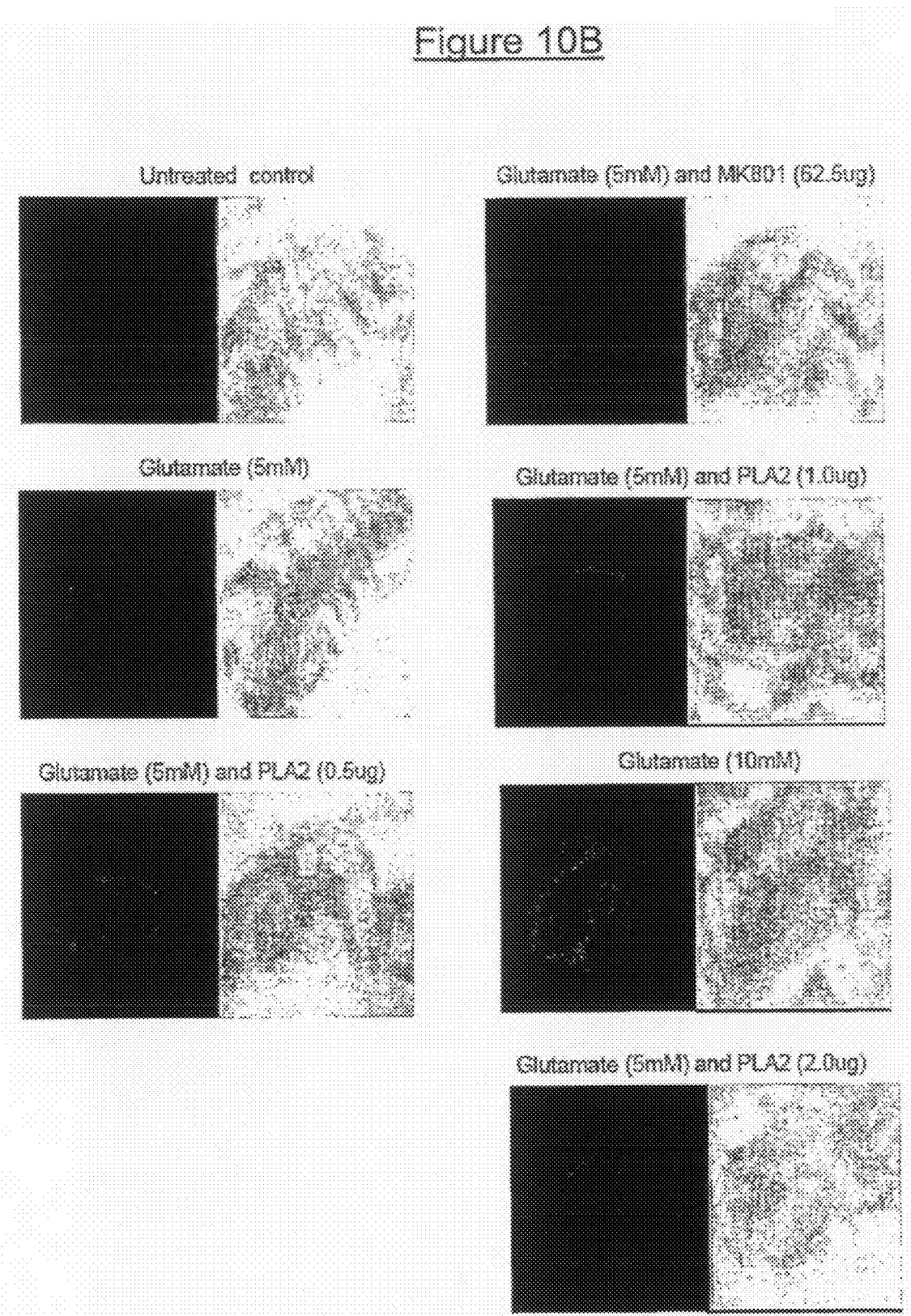

SEQUENCE LISTING

```
<160> NUMBER OF SEQ ID NOS: 3

<210> SEQ ID NO 1
<211> LENGTH: 469
<212> TYPE: DNA
<213> ORGANISM: Naja sputatrix
<220> FEATURE:
<221> NAME/KEY: CDS
<222> LOCATION: (96)..(452)
<223> OTHER INFORMATION: Phospholipase A2, mature peptide EC 3.1.1.4
<300> PUBLICATION INFORMATION:
<308> DATABASE ACCESSION NUMBER: L42005.1
<309> DATABASE ENTRY DATE: 1995-05-10
<313> RELEVANT RESIDUES IN SEQ ID NO: (96)..(452)
<300> PUBLICATION INFORMATION:
<308> DATABASE ACCESSION NUMBER: Q92085
<309> DATABASE ENTRY DATE: 2006-02-07
<313> RELEVANT RESIDUES IN SEQ ID NO: (28)..(146)

<400> SEQUENCE: 1
tcacctcgga caaaatgaat cctgctcacc ttctgatcct ggcagcagtt tgtgtctccc        60
ccttaggagc ctcctctaat cgtcccatgc ctctc aac ctc tat cag ttc aaa        113
                                    Asn Leu Tyr Gln Phe Lys
                                     1               5 aac atg gtt caa tgt act gtc ccc aat cga tct tgg tgg cat ttt gcg        161
Asn Met Val Gln Cys Thr Val Pro Asn Arg Ser Trp Trp His Phe Ala
            10                  15                  20 gac tac ggt tgc tac tgc gga cgc gga ggt agc ggg aca cca gta gac        209
Asp Tyr Gly Cys Tyr Cys Gly Arg Gly Gly Ser Gly Thr Pro Val Asp
        25                  30                  35 gac ttg gat agg tgc tgc cag att cat gac aac tgc tat aat gaa gct        257
Asp Leu Asp Arg Cys Cys Gln Ile His Asp Asn Cys Tyr Asn Glu Ala
    40                  45                  50 gaa aaa att tcc aga tgc tgg ccc tac ttc aag acc tat tca tac gag        305
Glu Lys Ile Ser Arg Cys Trp Pro Tyr Phe Lys Thr Tyr Ser Tyr Glu
55                  60                  65                  70 tgt tct caa ggc aca ctc acc tgc aaa ggt ggc aac aat gcg tgt gca        353
Cys Ser Gln Gly Thr Leu Thr Cys Lys Gly Gly Asn Asn Ala Cys Ala
                75                  80                  85 gct gct gtc tgt gat tgt gac cgc ttg gca gcc atc tgc ttc gcc gga        401
Ala Ala Val Cys Asp Cys Asp Arg Leu Ala Ala Ile Cys Phe Ala Gly
            90                  95                 100
```

```
gcc cct tac aac gat aac aac tac aat atc gac ctc aag gca cgt tgc    449
Ala Pro Tyr Asn Asp Asn Asn Tyr Asn Ile Asp Leu Lys Ala Arg Cys
        105                 110                 115 caa tgatatttga gaggcta                                              469
Gln
```

<210> SEQ ID NO 2
<211> LENGTH: 119
<212> TYPE: PRT
<213> ORGANISM: Naja sputatrix

<400> SEQUENCE: 2

```
Asn Leu Tyr Gln Phe Lys Asn Met Val Gln Cys Thr Val Pro Asn Arg
1               5                   10                  15

Ser Trp Trp His Phe Ala Asp Tyr Gly Cys Tyr Cys Gly Arg Gly Gly
            20                  25                  30

Ser Gly Thr Pro Val Asp Asp Leu Asp Arg Cys Cys Gln Ile His Asp
        35                  40                  45

Asn Cys Tyr Asn Glu Ala Glu Lys Ile Ser Arg Cys Trp Pro Tyr Phe
    50                  55                  60

Lys Thr Tyr Ser Tyr Glu Cys Ser Gln Gly Thr Leu Thr Cys Lys Gly
65                  70                  75                  80

Gly Asn Asn Ala Cys Ala Ala Val Cys Asp Cys Asp Arg Leu Ala
                85                  90                  95

Ala Ile Cys Phe Ala Gly Ala Pro Tyr Asn Asp Asn Asn Tyr Asn Ile
            100                 105                 110

Asp Leu Lys Ala Arg Cys Gln
        115
```

<210> SEQ ID NO 3
<211> LENGTH: 146
<212> TYPE: PRT
<213> ORGANISM: Naja sputatrix

<400> SEQUENCE: 3

```
Met Asn Pro Ala His Leu Leu Ile Leu Ala Ala Val Cys Val Ser Pro
1               5                   10                  15

Leu Gly Ala Ser Ser Asn Arg Pro Met Pro Leu Asn Leu Tyr Gln Phe
            20                  25                  30

Lys Asn Met Val Gln Cys Thr Val Pro Asn Arg Ser Trp Trp His Phe
        35                  40                  45

Ala Asp Tyr Gly Cys Tyr Cys Gly Arg Gly Gly Ser Gly Thr Pro Val
    50                  55                  60

Asp Asp Leu Asp Arg Cys Cys Gln Ile His Asp Asn Cys Tyr Asn Glu
65                  70                  75                  80

Ala Glu Lys Ile Ser Arg Cys Trp Pro Tyr Phe Lys Thr Tyr Ser Tyr
                85                  90                  95

Glu Cys Ser Gln Gly Thr Leu Thr Cys Lys Gly Gly Asn Asn Ala Cys
            100                 105                 110

Ala Ala Ala Val Cys Asp Cys Asp Arg Leu Ala Ala Ile Cys Phe Ala
        115                 120                 125

Gly Ala Pro Tyr Asn Asp Asn Asn Tyr Asn Ile Asp Leu Lys Ala Arg
    130                 135                 140

Cys Gln
145
```

PHOSPHOLIPASE(S) AND USE(S) THEREOF

FIELD OF THE INVENTION

The present invention is in the field of medicine. In particular, the present invention relates to phospholipase(s) and use(s) thereof.

BACKGROUND OF THE INVENTION

Stroke is the third most common cause of death globally after ischemic heart disease and all types of cancer combined. Although it sometimes affects children and young adults, stroke is mainly a disease of older people. Hence by 2020, stroke mortality would have almost doubled, mainly as a result of an increase in the proportion of aging population and the increase in other risk factors (Warlow et al., 2003).

Stroke is defined by WHO as the clinical syndrome of rapid onset of focal (or global) cerebral deficit, lasting more than 24 h or leading to death, with no apparent cause other than a vascular one. There are three pathological types: ischemic stroke, primary intracerebral haemorrhage and subarachnoid haemorrhage (Warlow et al., 2001). In haemorrhagic stroke, blood bursts through the walls of an artery and leaks into the brain (intracerebral haemorrhage) or onto the surface of the brain (subarachnoid haemorrhage).

Ischemic stroke results from a transient or permanent reduction in cerebral blood flow that is restricted to the territory of a major brain artery. The reduction in flow is, in a majority of the cases, due to an occlusion of a cerebral artery either by an embolus or by local thrombosis. Brain tissue is extremely sensitive to ischemia such that even a brief cessation of blood flow to cerebral neurons can initiate a complex sequence of events that ultimately culminate in cellular death. Different brain regions exhibit variable thresholds for ischemia, with white matter being more resilient than grey matter.

Additionally, certain populations of cerebral neurons are selectively vulnerable to ischemia, such as hippocampal CA1 cells and cerebral neurons as compared to dentate granule cells and brain stem neurons respectively (Smith, 2004). Ischemia of cerebral tissue and the ensuing cell death underlie all forms of stroke, including focal ischemia (reduction of nervous system blood supply to focal regions of the brain e.g. Middle cerebral artery (MCA), global ischemia (declining blood flow to entire cerebral hemisphere/s) and possibly, intraparenchymal hemorrhage (Karpiak et al, 1989; Smith, 2004).

Within minutes of focal vascular occlusion, brain tissue is deprived of glucose and oxygen, resulting in the accumulation of acidic by-products of metabolism. This loss of substrate and drop in pH leads to a cessation of the electron transport chain activity in the mitochondria and a rapid decline in ATP concentration. Loss of ATP eventually leads to failure of the $Na^+/K^+$-ATPase, which results in a marked increase of intracellular $Na^+$. Persistent depolarization allows $Ca^{2+}$ entry whilst a higher intracellular $Na^+$ concentration reduces the efficacy of the $2Na^+/Ca^{2+}$ symporter, further increasing intracellular $Ca^{2+}$ (Smith, 2004). Since membrane potential reaches the electrical threshold for discharge, neurons fire repetitively and release their neurotransmitters locally and at distant targets. Accumulation of glutamate in the extracellular space results in the activation of NMDA and metabotropic glutamate receptors, contributing to $Ca^{2+}$ overload. As a consequence of glutamate-mediated overactivation, Na+ and Cl⁻ enter neurons via channels for monovalent ions (eg. AMPA (alpha-amino-3-hydroxy-5-methyl-4-isoxazolepropionic acid) receptors). Water follows passively down an osmotic gradient and the ensuing edema can affect perfusion and give rise to increased intracranial pressure, vascular compression and herniation (Dirnagl et al, 1999). In fact, brain edema is one of the major determinants as to whether a patient survives beyond the first few hours after stroke.

An increase in the universal second messenger, $Ca^{2+}$, initiates a series of cytoplasmic and nuclear events that impact the development of tissue damage profoundly, such as activation of proteolytic enzymes that degrade cytoskeletal proteins like actin and spectrin (Furukawa et al, 1997), as well as extracellular matrix proteins like laminin (Chen and Strickland, 1997). Activation of cytosolic $PLA_2$ and cyclooxygenase generates free radical species that overwhelm endogenous scavenging mechanisms, producing lipid peroxidation and membrane damage (Zhao et al, 1994; Weisbrot-Lefkowitz et al, 1998). The importance of oxygen free radicals in cell damage associated with stroke is highlighted by the fact that even delayed treatment with free radical scavengers can be effective in experimental focal ischemia (Zhao et al, 1994).

Oxygen free radicals also serve as important signalling molecules that trigger inflammation. Mediators of inflammation, such as platelet-activating factor, TNF-a and IL-1β are produced by injured brain cells (Rothwell and Hopkins, 1995). Consequently, the expression of adhesion molecules on the endothelial cells surfaces is induced, promoting the migration of neutrophils into brain parenchyma. Macrophages and monoctyes follow, becoming the predominant cells in the ischemic brain five to seven days after the occurrence of stroke (Iadecola, 1997). Chemokines like IL-8 are produced by the injured brain and play key roles in chemotaxis of blood-borne inflammatory cells. Post-ischemic inflammation can contribute to ischemic damage by many mechanisms. The haemodynamic, metabolic and ionic changes described above do not affect the ischemic territory homogenously in the case of focal cerebral ischemia. Here, blood flow is most greatly reduced in a central region of the brain, known as the core, and in a graded manner centrifugally from the core, an area termed the penumbra (Hakim, 1987). Cerebral blood flow decreases to less than 15% of baseline within the core, whilst it is between 15% to 40% of baseline in penumbral regions. All neurons in the core will infarct if duration of ischemia is thirty minutes or more whereas only some in the penumbra will die, depending on the length of ischemia. By definition, the penumbra is that ischemic region that is functionally impaired but viable and potentially salvageable with timely therapeutic intervention (Schaller and Graf, 2004; Fisher, 2004). Hence, the process by which the penumbra is destroyed is the focus of most ischemic research as prevention of this infarct growth would be expected to rescue neuronal tissue.

Two strategies exist for reducing nerve cell death after ischemic insult: (a) insult limitation whereby blood flow is restored before infarction can occur (reperfusion) and (b) neuroprotection, which involves intervening to reduce specific mechanisms responsible for neuronal death thereby reducing the brain's intrinsic vulnerability to a given insult (Choi, 2000). A good example of insult limitation is the direct use of tissue plasminogen activator (tPA) to dissolve brain arterial blood clots. If accomplished within 3 hr of the onset of stroke symptoms, tPA is effective in improving clinical outcome (The National Institute of Neurological Disorders and Stroke rtPA Stroke Study Group, 1995) and is currently the only approved stroke therapy. To this end, defibrinogenating agents such as ancrod (Sherman et al, 2000) and thrombolytic agents like purokinase (Furlan et al, 1999) have been found to be capable of initiating reperfusion after ischemia, though neither has achieved regulatory approval.

Neuroprotection, on the other hand, is based on identifying and then blocking specific mechanisms involved in ischemic cell death. Two modes of cell death predominate after stroke, namely, necrosis and apoptosis. Necrosis takes place primarily in the core whilst apoptosis defines death in the penumbra or any region with less severe declines in cerebral blood flow (Ye et al, 2001). All previously performed pivotal trials of neuroprotective drugs have, however, failed to achieve a significant treatment effect on the pre-specified primary outcome measure (Fisher and Schaebitz, 2000).

Whilst the strategy of constraining cerebral ischemia through restoration of blood flow has almost reached the clinical trials, the identification of alternative and/or improved neuroprotective agents will be useful.

Currently, the only approved acute stroke therapy is intravenous recombinant tPA (tissue plasminogen activator) administration initiated within three hours of stroke onset. However, emerging data suggests that under some conditions, tPA can be potentially neurotoxic (Tsirka et al, 1997; Wang et al, 1998; Nagai et al, 2001). As such, there is a need to encompass newer approaches to intervention in this field of medicine.

SUMMARY OF THE INVENTION

The present invention addresses the problems above, and provides new and/or improved uses and methods in the field of medicine. In particular, the present invention relates to phospholipase(s) and use(s) thereof.

Accordingly, the present invention provides the use of at least one phospholipase, isoform, derivative, mutant and/or fragment thereof, for the preparation of a medicament for the treatment and/or prevention of ischemia. The phospholipase may be a secretory phospholipase or cytoplasmic phospholipase. The secretory phospholipase may be pancreatic, synovial and/or venomous phospholipase. According to a particular aspect, the phospholipase is a neutral venom phospholipase. In particular, the phospholipase is phospholipase $A_2$.

There is also provided the use according to the invention, wherein the phospholipase may be from snake venom. In particular, the snake venom may be from *Naja sputatrix* venom.

There is also provided the use according to the invention wherein the phospholipase may comprise the amino acid sequence of SEQ ID NO:2. In particular, the phospholipase isoform, derivative, mutant, and/or fragment thereof may be an isoform, derivative, mutant, and/or fragment thereof of a polypeptide comprising the amino acid sequence SEQ ID NO:2.

There is also provided the use according to the invention, wherein the phospholipase, isoform, derivative, mutant, and/ or fragment may comprise at least one amino acid substitution, addition, deletion, and/or at least one chemical modification.

There is also provided the use according to the invention, wherein the ischemia may be selected from the group consisting of cerebral ischemia, cardiac ischemia, and/or skeletal muscle ischemia. The ischemia may be cerebral ischemia.

The ischemia may also be transient focal ischemia.

There is also provided the use according to the invention, wherein the treatment may comprise inducing neuroprotective effects in a mammal at risk of ischemic stroke.

There is also provided the use according to the invention wherein the phospholipase according to any aspect of the invention reduces ischemic infarct size compared to tPA and/ or MK801.

There is also provided the use according to the invention, wherein the phospholipase according to any aspect of the invention reduces ischemic cell death compared to tPA and/or MK801. There is also provided the use according to any aspect of the invention, wherein administration of the medicament results in reduction of infarct size, decrease in gene expression of thyrotropin releasing hormone, decrease in gene expression of secreted phosphoprotein, decrease in gene expression of moesin, decrease in gene expression of metalloproteinase-9 (MMP-9), decrease in gene expression of tissue inhibitor of matrix metalloproteinase 1 (TIMP-1), decrease in gene expression of calgranulin A, increase in gene expression of glutathione-S-transferase, increase in gene expression of CAM kinase II, and/or increase in gene expression of angiotensinogen compared to the ischemic state.

There is also provided the use according to any aspect of the invention, wherein administration of phospholipase up-regulates at least one anti-apoptotic gene and/or gene transcript.

There is also provided the use according to any aspect of the invention, wherein administration of phospholipase down-regulates at lease one pro-apoptotic gene and/or gene transcript.

There is also provided the use according to the invention, wherein the treatment and/or prevention may comprise the steps of:
administering the medicament at least once and/or continuously before the onset of the ischemia;
administering the medicament at least once and/or continuously during the onset of the ischemia; and/or
administering the medicament at least once and/or continuously after the onset of the ischemia.

There is also provided the use according to the invention, wherein the phospholipase may be administered at least once and/or continuously, before the onset of the ischemia; and/or at least once and/or continuously, after the onset of the ischemia.

There is also provided the use according to the invention, wherein the phopholipase may be administered at least once and/or continuously, during the onset of the ischemia; and/or after the onset of the ischemia. In particular, the administration may be at least once and/or continuously, during and/or until 20 minutes after the onset of the ischemia. In particular, the administration may be at least once and/or continuously, during and/or until 15 minutes after the onset of the ischemia. More particularly, the administration may be at least once and/or continuously, during and/or until 10 minutes after the onset of the ischemia. More particularly, the administration may be at least once and/or continuously, during and/or until 1, 2, 3, 4, 5, 6, 7, 8, 9, 10, 11, 12, 13, 14 or 15 minutes after the onset of the ischemia. Even more in particular, until 5 minutes after the onset of the ischemia. There is also provided the use according to the invention, wherein the phospholipase may be further administered in combination and/or in succession with at least one neuroprotective compound different from the phospholipase. There is also provided the use according to the invention, wherein the medicament may further comprise at least one pharmaceutically acceptable excipient, diluent, carrier and/or adjuvant.

There is also provided the use according to the invention, wherein the medicament may be for the treatment and/or prevention of ischemia in a subject. The subject may be a mammal. In particular, the mammal is a human.

There is also provided the use according to any aspect of the invention, wherein the phospholipase, isoform, derivative, mutant and/or fragment thereof, e for use in the preparation of a medicament for the treatment and/or prevention of ischemia be from *Naja sputatrix* venom. In particular, the phospholipase is phospholipase $A_2$. There is also provided the use according to the invention, wherein the phospholipase may comprise the amino acid sequence of SEQ ID NO:2. The amino acid sequence of SEQ ID NO:2 may comprise at least one amino acid substitution, addition, deletion, and/or at least one chemical modification; and/or a fragment thereof.

There is also provided the use according to the invention, wherein the ischemia is cerebral ischemia. There is also provided a pharmaceutical composition comprising the phospholipase according to any aspect of the invention.

The present invention also provides a diagnostic kit for treatment and/or prevention of ischemia comprising the phospholipase, isoform, derivative, mutant and/or fragment thereof, according to any aspect of the invention.

The kit may further comprise at least one pharmaceutically acceptable excipient, diluent, carrier and/or adjuvant.

According to another aspect, the present invention provides a method for the treatment and/or prevention of ischemia comprising administering to a subject a therapeutically effective amount of phospholipase, derivative, mutant and/or fragment thereof. In particular, the phospholipase is a secretory phospholipase or cytoplasmic phospholipase. The secretory phospholipase may be pancreatic, synovial and/or venomous phospholipase. The phospholipase may be neutral venom phospholipase. The phospholipase may be from snake venom. In particular, the phospholipase may be from *Naja sputatrix* venom. Even more in particular, the phospholipase is phospholipase $A_2$.

There is also further provided a method for the treatment and/or prevention of ischemia comprising administering to a subject a therapeutically effective amount of at least one phospholipase, isoform, derivative, mutant and/or fragment thereof, wherein the phospholipase, isoform, derivative, mutant and/or fragment thereof is from *Naja sputatrix* venom.

There is also provided a method according to the invention, wherein the phospholipase comprises the amino acid sequence SEQ ID NO:2.

There is also provided a method according to the invention, wherein the phospholipase, an isoform, derivative, mutant, and/or fragment thereof comprises an isoform, derivative, mutant, and/or fragment thereof of a polypeptide that may comprise the amino acid sequence SEQ ID NO:2.

There is also provided a method according to the invention, wherein the phospholipase, isoform, derivative, mutant, and/or fragment comprises at least one amino acid substitution, addition, deletion, and/or at least one chemical modification.

There is also provided a method according to the invention, wherein the ischemia may be selected from the group consisting of cerebral ischemia, cardiac ischemia, and/or skeletal muscle ischemia. The ischemia may also be transient focal ischemia.

There is also provided a method according to the invention, wherein the treatment may comprise inducing neuroprotective effects in a mammal at risk of ischemic stroke.

There is also provided a method according to the invention, wherein the phospholipase reduces ischemic infarct size compared to tPA and/or MK801.

There is also provided a method according to the invention, wherein the phospholipase, isoform, derivative, mutant and/or fragment thereof, reduces ischemic cell death compared to tPA and/or MK801.

There is also provided a method according to the invention, wherein administration of phospholipase, isoform, derivative, mutant and/or fragment thereof results in reduction of infarct size, decrease in gene expression of thyrotropin releasing hormone, decrease in gene expression of secreted phosphoprotein, decrease in gene expression of moesin, decrease in gene expression of metalloproteinase-9 (MMP-9), decrease in gene expression of tissue inhibitor of matrix metalloproteinase 1 (TIMP-1), decrease in gene expression of calgranulin A, increase in gene expression of glutathione-S-transferase, increase in gene expression of CAM kinase II, and/or increase in gene expression of angiotensinogen compared to the ischemic state.

There is also further provided a method according to the invention, wherein administration of phospholipase $A_2$, an isoform, derivative, mutant and/or fragment thereof, up-regulates at least one anti-apoptotic gene and/or gene transcript. In particular, the anti-apoptotic gene may comprise Bcl-2 and/or Bcl-XL.

There is also provided a method according to the invention, wherein administration of phospholipase, an isoform, derivative, mutant and/or fragment thereof, down-regulates at least one pro-apoptotic gene and/or gene transcript. In particular, the pro-apoptotic gene may comprise Bax.

There is also provided a method according to the invention, wherein the treatment and/or prevention comprises administering the phospholipase isoform, derivative, mutant and/or fragment thereof:

at least once and/or continuously before the onset of the ischemia;

at least once and/or continuously during the onset of the ischemia; and/or at least once and/or continuously after the onset of the ischemia.

There is also provided a method according to the invention, wherein the phospholipase, isoform, derivative, mutant and/or fragment thereof, is administered before and/or after the onset of the ischemia.

There is also provided a method according to the invention, wherein the phospholipase, isoform, derivative, mutant and/or fragment thereof, is administered at least once and/or continuously, during and/or after the onset of the ischemia. In particular, the administration may be at least once and/or continuously, during and/or until 15 minutes after the onset of the ischemia. The administration may be at least once and/or continuously, during and/or until a suitable period as described above after the onset of the ischemia.

Particularly, the administration may be at least once and/or continuously during and/or until 14, 10 or 5 minutes after the onset of the ischemia.

There is also provided a method according to the invention, wherein the phospholipase, isoform, derivative, mutant and/or fragment thereof, is further administered in combination and/or in succession with at least one neuroprotective compound different from the phospholipase, isoform, derivative, mutant and/or fragment thereof.

There is also provided a method according to the invention, wherein the phospholipase, isoform, derivative, mutant and/or fragment thereof, is administered in conjunction with at least one pharmaceutically acceptable, excipient, diluent, carrier and/or adjuvant.

There is also further provided a method according to the invention, wherein the treatment and/or prevention of ischemia is administered to a subject. The subject may be a mammal. In particular, the mammal is a human.

BRIEF DESCRIPTION OF THE FIGURES

FIG. 1(A, B and C): Fractionation and purification of a $NsPLA_2$ from *Naja sputatrix* venom. Graph A: Sephadex G-50 gel filtration chromatography of 100 mg of *N. sputatrix* crude venom. Peak 1 (P1) contained the phospholipases. Graph B: The Sephadex G-50 gel filtration chromatography fractions containing PLA2 protein were pooled and subjected to RP-HPLC fractionation using Buffer A (0.1% TFA) and Buffer B (75% acetonitrile in 0.1% TFA). Graph C: The fractions containing a mixture of *N. sputatrix* PLA2 were pooled again and subjected to second RP-HPLC fractionation using Buffer A (0.1% TFA) and Buffer B (75% acetonitrile in 0.1% TFA); to obtain a homogeneous NsPLA2 of *N. sputatrix*.

FIG. 2: Laser doppler flowmetry. Cerebral blood flow was measured in the territory of the middle cerebral artery (MCA) pre-occlusion, immediately post-occlusion and during reperfusion.

FIG. 3 (A and B): Histopathological analysis of brain sections. (A) The photographs show serial coronal sections, for rostral to caudal slices stained with TTC. Surviving tissue stains red whilst dead cells remain white. The brain sections were obtained from rats treated with 30 μg/200 g body weight $NsPLA_2$ intravenously at 0-, 5-, 15-, 30-, 60 min post-occlusion. (B) Infarct volumes were quantitated using Scion Image software (Scion Corporation, USA) and significant protection from ischemic damage was seen when $NsPLA_2$ was administrated immediately after reversible MCAo (middle cerebral artery occlusion).

FIG. 4 (A and B): $NsPLA_2$ administered before reversible MCAo. (A): The photographs show serial coronal sections, for rostral to caudal slices stained with TTC (triphenyltetrazolium chloride). $NsPLA_2$ was injected intravenously 5 min pre-occlusion and brains were harvested 24 hr after the induction of stroke. (B): Infarct volumes were measured and no significant difference was found in the insult size between the saline- and $NsPLA_2$-treated brains.

FIG. 5 (A and B): Administration of tPA and MK801. (A): Rats were subjected to reversible focal ischemia and tPA (tissue plasminogen activator) 10 mg/kg body weight; infusion was initiated intravenously, 30 min post-occlusion. Alternatively, MK801 (dizocilpine) was injected intraperitoneally in three doses: 2.5 mg/kg, 30 min prior to MCAo followed by 1.25 mg/kg, 6 hr and 14 hr post-occlusion. Extensive damage was observed in both control and tPA-treated brain whilst MK801 conferred neuroprotection. (B): Infarct volumes were determined and a significant reduction in infarct size could be seen in MK801—but not in tPA-treated brains.

FIG. 6 (A to F): Histological analysis of paraffin-embedded brain sections. Whole, unperfused brains were sectioned and stained with haematoxylin and eosin. High power (×120) photomicrographs of striatal (A to C) and cortical (D to F) tissues were examined. Sham-operated brains showed healthy tissue (A and D) whilst the induction of focal ischemia for 1 hr caused severe neuronal damage, resulting in nuclear pleomorphism and pyknosis (B and E). Intravenous administration of 30 μg/200 g body weight $NsPLA_2$ immediately post-occlusion protected neurons from ischemic damage and reduced tissue injury (C and F). Nuclei of damaged (B and E) and healthy (C and F) cells are indicated by arrows.

FIG. 7(A to F): TUNEL detection of neuronal cell death. Enzymatic labeling of free 3'-OH termini is a useful method of determining cell death by apoptosis, which gives rise to cleaved DNA. Whole, unperfused brains were sectioned and stained to determine the extent of cell death in the striatum (A to C, x120) and cortex (D to F, x120) of sham-operated (A and E), MCA-occluded (B and E), and $NsPLA_2$-treated (C and F) rats. There was no observable cell death in sham-operated brains (nuclei stained bluish green in live cells) but extensive neuronal apoptosis was seen in brains of rats subjected to reversible focal ischemia (nuclei stained brown). Almost no live cells could be found. Treatment with 30 μg/200 g body weight $NsPLA_2$ at 0 min after MCA occlusion protected neurons from ischemic cell death. Apoptotic nuclei are indicated by arrows and results are representative of 3 independent experiments.

FIG. 8(A and B): Quantitative real-time PCR analysis. Validation of microarray data for the expression of 9 genes in sham-operated, MCAo and $NsPLA_2$-treated brains was carried out using realtime PCR. (A) All genes were significantly upregulated by ischemia except for glutathione-S-transferase, CAM kinase II and angiotensinogen. (B) $NsPLA_2$ treatment immediately post-occlusion led to a significant decrease in the expression of genes upregulated by ischemia and vice versa for those that were down-regulated.

FIG. 9: Determination of TNF-a levels in the serum of rats. Adult Sprague-Dawley rats (n=3) were either treated intravenously with lipopolysaccharide (LPS), saline and 30 μg/200 g body weight $NsPLA_2$ alone or were subjected to transient focal ischemia before administration of saline or $NsPLA_2$ immediately post-occlusion. LPS-treated rats had significantly increased TNF-a levels in their serum after 1 hr whilst only basal concentrations were detected in the serum of saline and $NsPLA_2$-treated rats.

FIG. 10 (A to C): Neuroprotection conferred by $NsPLA_2$ upon glutamate neurotoxicity in organotypic hippocampal culture, (during the glutamate insult, concurrent and during the recovery period, post-treatment). Organotypic hippocampal cultures were subjected to glutamate insults for 3 hours and treated with $NsPLA_2$ (A) during insult (B) during recovery. In both conditions, the $NsPLA_2$ protected the hippocampal tissues from glutamate induced neurotoxicity. (C) Cytotoxicity assay (lactose dehydrogenase (LDH) assay) showed that the $NsPLA_2$ treatment reduced the cell death experienced by the hippocampal tissues.

FIG. 11: Neuroprotection conferred by $NsPLA_2$ during glutamate receptor ligand (NMDA, KA and AMPA) mediated neurotoxicity. Organotypic hippocampal cultures were subjected to NMDA (N-methyl-D-aspartate), KA (kainic acid) and AMPA (alpha-amino-3-hydroxy-5-methyl-4-isoxazolepropionic acid) insults for 3 hours and treated with $NsPLA_2$ concurrently. The $NsPLA_2$ protected the hippocampal tissues from the induced neurotoxicity.

FIG. 12 (A and B): Neuroprotection conferred by $NsPLA_2$ in OGD culture. (A) Organotypic hippocampal cultures were subjected to OGD (oxygen-glucose deprivation) for 90 mins and treated with $NsPLA_2$. The $NsPLA_2$ protected the hippocampal tissues from the ischemic induced cell death. (B) Realtime PCR results on anti- or pro-apoptotic (Bcl-2, Bcl-XL and Bax) genes during OGD (oxygen-glucose deprivation) and $NsPLA_2$ treatment. Total RNA was isolated from the hippocampal tissues and subjected to reverse transcription and PCR. The data was derived from 6 independent PCR (n=6). Both the anti-apoptotic genes, Bcl-2 and Bcl-XL were upregulated while the pro-apoptotic (Bax) gene was down-regulated.

BRIEF DESCRIPTION OF TABLES

Table 1: List of genes whose expression was changed by $NsPLA_2$ treatment when compared to saline-treated MCAo controls. These genes were also differentially expressed in MCAo (middle cerebral artery occlusion) brains relative to those in sham-operated ones. Fold changes greater or equal to 1.7 were deemed significant. Gene ID—Affymetrix identification number; F.C.—fold change.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

Accordingly, the present invention provides a use of at least one phospholipase, isoform, derivative, mutant and/or fragment thereof, for the preparation of a medicament for the treatment and/or prevention of ischemia.

According to any aspect of the present invention, the at least one phospholipase may be a secretory phospholipase or cytoplasmic phospholipase. The secretory phospholipase may be pancreatic, synovial and/or venomous phospholipase. The phospholipase may be a neutral venom phospholipase. In particular, the phospholipase may be from Naja venom. For example, the phospholipase may be from *Naja sputatrix* venom. Even more in particular, the phospholipase may be phospholipase $A_2$. The phospholipase $A_2$ may be selected from any one of Group I to Group XI phospholipase $A_2$.

According to any aspect of the present invention, phospholipase may also include phospholipase from all types, isoforms, derivatives, groups, and subgroups of phospholipases, including but not limited to phospholipase $A_1$, phospholipase $A_2$, phospholipase B, phospholipase C or phospholipase D.

Phospholipase $A_1$ (E.C.3.1.1.32) catalyses the hydrolysis of phosphatidylcholineto 2-acylglycerophosphocholine and a fatty acid anion. Phospholipase B is said to be a mixture of both $PLA_1$ and $PLA_2$. It generally acts on lysolecithin (which is formed by the action of $PLA_2$ on lecithin). The action of Phospholipase B results in the cleaving of both fatty acid residues. lysophospholipase (E.C. 3.1.1.5). Phospholipase C (PDB 1AH7, EC 3.1.4.3) is a key enzyme in phosphatidylinositol ($PIP_2$) metabolism and lipid signaling pathways. It converts phosphatidylinositol to inositol triphosphate ($IP_3$) and diacylglycerol (DAG). They all require calcium for catalytic activity. It is activated by either Gaq protein (making it part of a G protein-coupled receptor signal transduction pathway) or by transmembrane receptors with intrinsic or associated tyrosine kinase activity. These can act on other proteins in cells to increase activity of enzymes, e.g. protein kinase C, or on membrane channels such as calcium channels in the sarcoplasmic reticulum in smooth muscle. The Phospholipase C family consists of PLC-d, -β, -γ and -e. Phospholipase D (EC 3.1.4.50) is located in the plasma membrane and catalyzes the hydrolysis of phosphatidylcholine to form phosphatidic acid (PA) and release choline headgroup. The phosphatidic acid may itself act as a signal molecule (e.g., by activating a PA-activated kinase), or can be hydrolyzed to form diacylglycerol (DAG) by the enzyme PA phosphohydrolase.

Accordingly, the phospholipase, isoform, derivative, mutant and/or fragment thereof according to the invention may be from snake venom. In particular, the phospholipase, isoform, derivative, mutant and/or fragment thereof is from *Naja sputatrix* venom. The phospholipase may comprise the amino acid sequence of SEQ ID NO:2. The phospholipase isoform, derivative, mutant, and/or fragment thereof may be a isoform, derivative, mutant, and/or fragment thereof of a polypeptide comprising the amino acid sequence of SEQ ID NO:2. The phospholipase, isoform, derivative, mutant, and/or fragment may comprise at least one amino acid substitution, addition, deletion, and/or at least one chemical modification.

Secreted phospholipases (secretory phospholipases) are classified according to sequence identity, and belong to three major collections of enzymes; Group I/II/V/X $sPLA_2$ collection e.g. *N. atra, Naja naja atra* $sPLA_2$; *C. atrox, Crotalus atrox* $sPLA_2$. *N. atra*, notexin, *C. atrox*, crotoxin, vipoxin, *C. major* and *D. labrax, Chrysophrys major* (red sea bream) and *Dicentrarchus labrax* (sea bass) $sPLA_2$, the second collection includes Group III $sPLA_2$s, e.g. IptX1, phospholipin, PA-2, PA-5, and bee venom/bumblebee $sPLA_2$s, and the third collection includes plant $sPLA_2$s, e.g. *A. thaliana, Arabidopsis thaliana* $sPLA_2$s; *D. caryophyllus, Dianthus caryophyllus* (carnation) $sPLA_2$; *M. truncatula, Medicado truncatula* (barrel medic.) $sPLA_2$; *P. taeda, Pinus taeda* (pine tree) $sPLA_2$; *P. tremula, Populus tremula* (poplar tree) $sPLA_2$. (Valentin et al). Secreted phospholipases may include synovial, pancreatic and/or venomous phospholipases.

Synovial $sPLA_2$ is a secreted phospholipase $A_2$ which is isolated from synovial fluid, which is defined as a clear, viscid substance formed as a diasylate, containing protein. Cells of the intima and the vascular and lymphatic plexus in the subintima secrete synovial fluid. These are found in synovial joints, bursae, and tendon sheaths. The joint cavity is lined with a synovial membrane. This membrane secretes synovial fluid that acts as a joint lubricant (Ombregt et al. 2003). Synovial sPLA2 is isolated from this synovial fluid, for example mammalian Group IIA $PLA_2$. Other secreted $PLA_2$ ($sPLA_2$) is a phospholipase $A_2$ enzyme that is expressed in an extracellular secretion, for example, mammalian pancreatic $sPLA_2$, (e.g. human, bovine, rat, canine), mammalian synovial $sPLA_2$, and venom $sPLA_2$ (e.g. from bee, snakes, crotalids and elapids). In particular, secreted $PLA_2$ may be from venom from *Naja sputatrix* (SEQ ID NO:2).

Cytoplasmic phospholipase may include cytosolic $PLA_2$ ($cPLA_2$). This is a phospholipase $A_2$ enzyme that is expressed in the cytoplasm, for example from neutrophils and platelets.

The phospholipase may be from venom, which may be classified as neutral venom or acidic venom. Accordingly, phospholipase from neutral venom is referred to as neutral phospholipase, while phospholipase from acidic venom is referred to as acidic phospholipase. For example, an acidic $PLA_2$ isozyme is characterized as having at least one neutral or basic amino acid substituted with an acidic amino acid. For example, in the acidic phospholipase $A_2$ isozyme from *Naja sputatrix* characterized in Armugam et al., 1997, one basic and one neutral amino acid (histidine and asparagine respectively) were substituted with two aspartic acid (acidic amino acid) residues.

For example, a neutral venom phospholipase $A_2$ is characterized as having no overall acidic or basic charge. A basic venom phospholipase $A_2$ is characterized as having an overall basic charge. A basic venom phospholipase is not as favourable for clinical use because the basicity of $PLA_2$s is found to be usually correlated with their toxicity. It appears that the positively charged residues increase the enzyme penetrability into the membranes which is important for further hydrolysis of phospholipids and, thus, for the pharmacological potency (Kini, 1997).

The phospholipase $A_2$ ($PLA_2$) superfamily is defined as a broad range of enzymes with the ability to catalyze the hydrolysis of the middle (sn-2) ester bond of substrate phospholipids.

An enzyme is assigned to a phospholipase $A_2$ group according to four criteria, the first essential criterion being that it must catalyze the hydrolysis of the sn-2 ester bond of a phospholipid substrate. Naturally occurring substrates include platelet activating factor, short fatty acid chain oxidized phospholipids, and long fatty acid chain phospholipids, with sn-2 acyl chains ranging from two (acetyl) to 20 carbons (arachidonate) and even longer. While the major activity must be $PLA_2$ activity, members of the $PLA_2$ superfamily may possess other activities, such as $PLA_1$, lysophospholipase $A_1/A_2$, acyl transferase, or transacylase activity.

The second essential criterion for an enzyme to be assigned to a $PLA_2$ Group is that the complete amino acid sequence for the mature protein is known. Future additions to the $PLA_2$ superfamily should be cloned, expressed, and purified to correlate the sequence to specific activity in an unambiguous system, regardless of whether they are discovered by DNA- or activity-based searches.

The third criterion for the classification is that each $PLA_2$ group should include all of those enzymes which have readily identifiable sequence homology. Specifically, if more than one homologous $PLA_2$ gene exists within a species (paralogs), then each $PLA_2$ gene is assigned a subgroup letter, as in the case of Groups IVA, IVB, and IVC $PLA_2$. It is also possible that paralogs will exist only in certain species, as is the case with Group IIC $PLA_2$. Homologs from different species (orthologs) are classified within the same subgroup wherever such assignments are possible, such as for zebra fish and human Group IVA $PLA_2$.

The fourth criterion for classification considers active splice variants of the same $PLA_2$ gene to be distinct proteins, but part of the same subgroup. Each splice variant with confirmed activity is numbered, for example, for Group VIA $PLA_2$, which has two confirmed, active splice variants, referred to as Group VIA-1 $PLA_2$ and Group VIA-2 $PLA_2$. For inactive splice variants, for example in the case of Group VIA $PLA_2$, the variants are referred to not as $PLA_2$ enzymes, but still using the Group nomenclature, as Group VIA Ankyrin-1 and Group VIA Ankyrin-2.

The abbreviation G for Group (i.e., GIAPLA$_2$ for Group IA PLA$_2$) is employed henceforth.

Phospholipase $A_2$ may be defined as an enzyme, comprising a polypeptide which is characterised by an amino acid sequence which is coded for by a phospholipase $A_2$ gene. Particularly, phospholipase $A_2$ may be defined as an enzyme comprising an amino acid sequence corresponding to SEQ ID NO:2, which is coded for by a phospholipase $A_2$ gene, which comprises a nucleic acid sequence corresponding to SEQ ID NO:1. More particularly, it may be defined as an enzyme that catalyses the hydrolysis of phospholipids, and is of the enzyme class EC 3.1.1.4.

In a further aspect, phospholipase $A_2$ ($PLA_2$) may be from other organisms, in particular pancreatic and secretory $PLA_2$ from mammals (e.g. human, bovine, rat, canine), or from bee and other venoms. Secreted $PLA_2$ ($sPLA_2$) is a phospholipase $A_2$ enzyme that is expressed in an extracellular secretion, for example, mammalian pancreatic $sPLA_2$, (e.g. human, bovine, rat, canine), mammalian synovial $sPLA_2$, and venom $sPLA_2$ (e.g. from bee, snakes, crotalids and elapids). In particular, secreted $PLA_2$ may be from venom from *Naja sputatrix* (SEQ ID NO:2).

Cytoplasmic or cytosolic $PLA_2$ ($cPLA_2$) is a phospholipase $A_2$ enzyme that is expressed in the cytoplasm, for example from neutrophils and platelets. Cytosolic PLA2 has been shown to be important for macrophage production of inflammatory mediators, fertility, and in the pathophysiology of neuronal death after local cerebral ischemia (Bonventre et al., 1997). An isoform, derivative, mutant and/or fragment of phospholipase may be defined as at least one polypeptide with an amino acid sequence substantially identical with phospholipase, with conserved amino acid changes that may be made without altering the function of the phospholipase according to the invention.

Particularly, it is within the knowledge of a skilled person how to make amino acid substitutions, for example at least one conservative amino acid substitution without altering the phospholipase biological, pharmaceutical and/or therapeutic activity. In particular, a "conservative amino acid substitution" is one in which the amino acid residue is replaced with an amino acid residue having a similar side chain. Families of amino acid residues having similar side chains have been defined in the art. These families include hydrophobic, hydrophilic, basic and acid amino acids as described below. Thus, a predicted non-essential amino acid residue in the peptide of the invention is preferably replaced with another amino acid residue from the same category. For example, a hydrophobic amino acid is replaced by another hydrophobic amino acid, etc.

A "non-essential" amino acid residue is a residue that can be altered from the wild-type sequence of a phospholipase without abolishing or substantially altering the phospholipase activity. Preferably the alteration does not substantially alter the phospholipase activity, e.g., the activity is at least 20%, 40%, 60%, 70% or 80% of wild-type. An "essential" amino acid residue is a residue that, when altered from the wild-type sequence of a phospholipase, results in abolishing phospholipase activity such that less than 20% of the wild-type activity is present. For example, conserved amino acid residues in between the phospholipase, e.g., the phospholipases as described in Jeyaseelan et al. (2000) are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Hydrophobic" amino acids are: A, V, L, I, P, W, F and M; "hydrophilic" amino acids are: G, S, T, Y, C, N and Q; however Y has a hydrophobic aromatic group and may be considered to be acting as a hydrophobic amino acid depending on the circumstances and uses; "basic" amino acids are: K, R and H; and "acidic" amino acids are: D and E.

Alternatively, in another embodiment, mutations can be introduced randomly along all or part of the coding sequence of the nucleic acid encoding the peptide of the invention, such as by saturation mutagenesis, and the resultant mutants can be screened for anticoagulant activity to identify mutants that retain that activity.

Thus, a predicted non-essential amino acid residue in a phospholipase protein is preferably replaced with another amino acid residue from the same side chain family. Alternatively, in another embodiment, mutations can be introduced randomly along all or part of a phospholipase coding sequence, such as by saturation mutagenesis, and the resultant mutants can be screened for phospholipase biological activity to identify mutants that retain activity. For example, following mutagenesis of SEQ ID NO: 1, the encoded protein can be expressed recombinantly and the activity of the protein can be determined.

Amino acid residues can be generally sub-classified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterises certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the .alpha.-amino group, as well as the .alpha.-carbon.

Several amino acid similarity matrices (e.g., PAM120 matrix and PAM250 matrix as disclosed for example by Dayhoff et al. (1978) A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., 1992, Science 256 (5062): 144301445), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or noncyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

The gene-encoded secondary amino acid proline is a special case due to its known effects on the secondary conformation of peptide chains, and is not, therefore, included in a group.

The "modified" amino acids that may be included in the phospholipases are gene-encoded amino acids which have been processed after translation of the gene, e.g., by the addition of methyl groups or derivatisation through covalent linkage to other substituents or oxidation or reduction or other covalent modification. The classification into which the resulting modified amino acid falls will be determined by the characteristics of the modified form. For example, if lysine were modified by acylating the .epsilon.-amino group, the modified form would not be classed as basic but as polar/large.

Certain commonly encountered amino acids, which are not encoded by the genetic code, include, for example, .beta.-alanine (.beta.-Ala), or other omega-amino acids, such as 3-aminopropionic, 2,3-diaminopropionic (2,3-diaP), 4-aminobutyric and so forth, .alpha.-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); .beta.-2-thienylalanine (Thi); methionine sulfoxide (MSO); and homoarginirie (Har). These also fall conveniently into particular categories.

Based on the above definitions, Sar, beta-Ala and Aib are small; t-BuA, t-BuG, N-MeIle, Nle, Mvl, Cha, Phg, NaI, Thi and Tic are hydrophobic; 2,3-diaP, Orn and Har are basic; Cit, Acetyl Lys and MSO are neutral/polar/large. The various omega-amino acids are classified according to size as small (.beta.-Ala and 3-aminopropionic) or as large and hydrophobic (all others).

Other amino acid substitutions for those encoded in the gene can also be included in SLEs within the scope of the invention and can be classified within this general scheme according to their structure.

In a further aspect, the phospholipase may comprise a "biologically active portion" of a phospholipase, which is defined as including a fragment of a phospholipase protein, which participates in an interaction, e.g., an intra-molecular or an inter-molecular interaction. An inter-molecular interaction can be a specific binding interaction or an enzymatic interaction (e.g., the interaction can be transient and a covalent bond is formed or broken). An inter-molecular interaction can be between a phospholipase molecule and a non-phospholipase molecule, (e.g. phosphatidylcholine), or between a first phospholipase molecule, (e.g., a light chain of a phospholipase) and a second phospholipase molecule (e.g., a dimerization interaction). Biologically active portions of a phospholipase protein include peptides comprising amino acid sequences sufficiently homologous to or derived from the amino acid sequence of the phospholipase protein, e.g., the amino acid sequence shown in SEQ ID NO:3, which includes less amino acids than the full length phospholipase proteins, and exhibits at least one activity of a phospholipase protein. Typically, biologically active portions comprise a domain or motif with at least one activity of the phospholipase protein, e.g., the ability to process phosphatidylcholine to 1-acylglycerophosphocholine and a carboxylate, e.g., in the absence of calcium and/or phospholipid. A biologically active portion of a phospholipase protein can be a polypeptide which is, for example, 10, 25, 50, 100, 200 or more amino acids in length. Preferably, said fragment is a "biologically-active portion" having no less than 1%, preferably no less than 10%, more preferably no less than 25% and even more preferably no less than 50% of the phosphatidylcholine, phosphatidylethanolamine, choline plasmalogen and/or phosphatides processing activity of at least one phospholipase described herein.

There is provided a "fragment" of a phospholipase of the invention. The term "fragment" includes within its scope heavy and light chain fragments of a phospholipase.

Snake venom may be defined as crude venom extract from a species of snake. Particularly, the species may be *Naja sputatrix*.

The ischemia according to the invention may be selected from the group consisting of cerebral ischemia, cardiac ischemia, and/or skeletal muscle ischemia. In particular, the ischemia may be cerebral ischemia. The ischemia may also be transient focal ischemia.

Ischemia may be defined as a restriction in blood supply, generally due to an occlusion of a blood vessel, which may be due to an embolus or local thrombosis. Ischemia is a feature of ischemic stroke, heart diseases, transient ischemic attacks, cerebrovascular accidents, ruptured arteriovenous malformations, and peripheral artery occlusive disease.

Ischemia may be further defined as an absolute or relative shortage of the blood supply to an organ. Relative shortage means the mismatch of blood supply (oxygen delivery) and blood request for adequate oxygenation of tissue. In particular, cerebral ischemia may be defined as the absolute or relative shortage of blood supply to the brain, and the tissue may be comprised of neurons. Cardiac ischemia may be defined as the absolute or relative shortage of blood supply to the heart, and the tissue may be comprised of cardiac tissue. Skeletal muscle ischemia may be defined as the absolute or relative shortage of blood supply to the skeletal muscles, and the tissue may be comprised of muscle tissue.

Transient focal ischemia may be defined as the transient and/or temporary reduction in blood flow of one blood vessel. In another aspect, transient multifocal ischemia may be subject to the treatment according to the invention, wherein there is a transient reduction in blood flow of more than one blood vessel.

The treatment according to the invention may comprise inducing neuroprotective effects in a mammal at risk of ischemic stroke. Neuroprotective effects may be described as the blockage of specific mechanisms involved in ischemic cell death, i.e. inhibiting apoptosis. In particular, neuroprotective effects may include Intervention to reduce specific mechanisms responsible for neuronal death thereby reducing the brain's intrinsic vulnerability to a given insult.

The use provided according to any aspect of the present invention may comprise the use of phospholipase, isoform, derivative, mutant and/or fragment thereof, to reduce ischemic infarct size compared to tPA and/or MK801. Ischemic infarct may be defined as ischemic infarction. Ischemic infarct may be defined as the region of ischemic tissue that is functionally impaired but viable and potentially salvageable with treatment. In particular, the region of ischemic tissue may be neural tissue. The region may be further defined as the penumbra or any region with less severe decline in blood flow, which may be defined as the region of tissue that has between 15% to 40% cerebral blood flow during ischemia.

The use provided may comprise the phospholipase according to the invention wherein the phospholipase, isoform, derivative, mutant and/or fragment thereof, reduces ischemic cell death compared to tPA and/or MK801. Ischemic cell death may be defined as the total number of cells that undergo apoptosis in the penumbra or any region with less severe decline in blood flow, and may be quantitatively measured as detailed in the examples, with a cytotoxicity assay, the method being well known to a skilled person in the art.

tPA may be defined as tissue plasminogen activator, which induces thrombolysis, in particular tPA dissolves blood clots. MK801 may be defined as dizocilpine, an NMDA (N-methyl-D-aspartate) antagonist.

The use provided may comprise the administration of phospholipase, isoform, derivative, mutant and/or fragment thereof, to a subject which may result in the reduction of infarct size, decrease in gene expression of thyrotropin releasing hormone, decrease in gene expression of secreted phosphoprotein, decrease in gene expression of moesin, decrease in gene expression of metalloproteinase-9 (MMP-9), decrease in gene expression of tissue inhibitor of matrix metalloproteinase 1 (TIMP-1), decrease in gene expression of calgranulin A, increase in gene expression of glutathione-S-transferase, increase in gene expression of CAM kinase II, and/or increase in gene expression of angiotensinogen compared to the ischemic state. The decrease and increase in gene expression may be obtained through a quantitative real-time PCR analysis as detailed in the examples, the general method being well known to a person skilled in the art.

The use provided may comprise the administration of phospholipase, isoform, derivative, mutant and/or fragment thereof, wherein at least one anti-apoptotic gene and/or gene transcript may be up-regulated. Particularly, the anti-apoptotic gene may be Bcl-2 and/or Bcl-XL. The use provided may comprise the administration of phospholipase, isoform, derivative, mutant and/or fragment thereof, wherein at least one pro-apoptotic gene and/or gene transcript may be down-regulated. Particularly, the pro-apoptotic gene may be Bax. The up-regulation and/or down-regulation of anti- and pro-apoptotic genes respectively may be observed by a real-time PCR analysis as detailed in the examples, the general method being well known to a person skilled in the art.

The use provided wherein the treatment and/or prevention may comprise the steps of:
administering the medicament at least once and/or continuously before the onset of the ischemia;
administering the medicament at least once and/or continuously during the onset of the ischemia; and/or
administering the medicament at least once and/or continuously after the onset of the ischemia.

The use provided wherein the phospholipase, isoform, derivative, mutant and/or fragment thereof, may be administered:
at least once and/or continuously, before, and/or after the onset of the ischemia;
at least once and/or continuously, during and/or after the onset of the ischemia; and/or
at least once and/or continuously, during and/or until about 20 minutes after the onset of the ischemia.

In particular, at least once and/or continuously, during and/or until about 15 minutes after the onset of the ischemia; at least once and/or continuously during and/or until about 14 minutes after the onset of the ischemia; for example, at least once and/or continuously during and/or until about 10 minutes after the onset of the ischemia; in particular, at least once and/or continuously during and/or until about 5 minutes after the onset of the ischemia;

According to one aspect of the invention, there is provided the use wherein the at least one phospholipase, isoform, derivative, mutant and/or fragment thereof, may be administered at least once and/or continuously during and/or until around 5 minutes after the onset of the ischemia. In particular, the phospholipase, isoform, derivative, mutant and/or fragment thereof may be administered at 0 minutes, at around 1 minute, at around 2 minutes, at around 3 minutes, at around 4 minutes and at around 5 minutes, continuously or at any instant of time in between 0 and around 5 minutes.

The use according to the present invention provides the phospholipase, isoform, derivative, mutant and/or fragment thereof, in particular, the phospholipase $A_2$, isoform, derivative, mutant and/or fragment thereof, may be further administered in combination and/or in succession with at least one a neuroprotective compound different from the phospholipase, isoform, derivative, mutant and/or fragment thereof. Neuroprotective compound may include any known agents capable of initiating reperfusion after ischemia, particularly defibrinogenating agents and/or thrombolytic agents. More particularly, tissue plasminogen activator (tPA), ancrod and/or purokinase.

According to any aspect of the present invention, the medicament may further comprise at least one pharmaceutically acceptable, excipient, diluent, carrier and/or adjuvant.

The medicament may be for the treatment and/or prevention of ischemia in a subject. The subject may be a mammal. In particular, the mammal may be a human.

The present invention also provides at least one isolated phospholipase, isoform, derivative, mutant and/or fragment thereof, for use in the treatment and/or prevention of ischemia. The phospholipase may be from venom. For example, the phospholipase may be a neutral venom phospholipase. In particular, the phospholipase may be from Naja venom. Even more in particular, from *Naja sputatrix* venom. In particular, the phospholipase may be phospholipase $A_2$, wherein the phospholipase, isoform, derivative, mutant and/or fragment thereof is from venom. The phospholipase may be a neutral venom phospholipase. In particular, the phospholipase may be from *Naja* venom. Even more in particular, from *Naja sputatrix* venom.

The at least one isolated phospholipase may be a secretory phospholipase or cytoplasmic phospholipase. The secretory phospholipase may be pancreatic, synovial and/or venomous phospholipase. The phospholipase may be a neutral venom phospholipase. In particular, the phospholipase may from Naja venom. For example, the phospholipase may be from *Naja sputatrix* venom. Even more in particular, the phospholipase may be phospholipase $A_2$. The phospholipase $A_2$ may be selected from any one of Group I to Group XI phospholipase $A_2$.

The at least one isolated phospholipase comprises the amino acid sequence of SEQ ID NO:2. The amino acid sequence of SEQ ID NO:2 may comprise at least one amino acid substitution, addition, deletion, and/or at least one chemical modification; and/or a fragment thereof.

The ischemia may be cerebral ischemia, cardiac ischemia, and/or skeletal muscle ischemia. In particular, the ischemia may be cerebral ischemia. The ischemia may also be transient focal ischemia.

The present invention also provides a pharmaceutical composition, which may comprise the phospholipase according to any aspect of the invention.

The pharmaceutical composition may further comprise at least one pharmaceutically acceptable carrier, diluent, adjuvant, excipients, or a combination thereof. Examples of suitable excipients are water, saline, dextrose, glycerol, ethanol and the like as well as combinations thereof. Such a pharmaceutical composition may consist of the active ingredient alone, in a form suitable for administration to a subject, or alternatively the pharmaceutical composition may comprise the active ingredient and one or more pharmaceutically acceptable carrier, excipient and/or diluent. Excipients normally employed for such formulations, includes mannitol, lactose, starch, magnesium stearate, sodium saccharine, cellulose, magnesium carbonate, and the like.

The pharmaceutical composition may be for local, subcutaneous, intravenal, parenteral and/or oral administration. The pharmaceutical composition may be administered through subcutaneous and/or intramuscular injection. For oral administration, the pharmaceutical composition may be formulated as solutions, suspensions, emulsions, tablets, pills, capsules, sustained release formulations, aerosols, powders, or granulates. The dosage required depends on the choice of the route of administration; the nature of the formulation; the nature of the subject's illness; the subject's size, weight, surface area, age, and sex; other drugs being administered; and the judgment of the attending physician. Wide variations in the needed dosage are to be expected in view of the variety of compounds available and the different efficiencies of various routes of administration.

The present invention also provides a diagnostic kit for treatment and/or prevention of ischemia comprising the phospholipase, isoform, derivative, mutant and/or fragment thereof, as described above. The phospholipase may be a secretory phospholipase or cytoplasmic phospholipase. The secretory phospholipase may be pancreatic, synovial and/or venomous phospholipase. The phospholipase may be a neutral venom phospholipase. In particular, the phospholipase may be from *Naja* venom. For example, the phospholipase may be from *Naja sputatrix* venom. Even more in particular, the phospholipase may be phospholipase $A_2$. The phospholipase $A_2$ may be selected from any one of Group I to Group XI phospholipase $A_2$. According to a particular aspect, there is provided a diagnostic kit for treatment and/or prevention of ischemia comprising the phospholipase $A_2$, isoform, derivative, mutant and/or fragment thereof, as described in the invention.

The kit according to any aspect of the present invention may further comprise at least one pharmaceutically acceptable excipient, diluent, carrier and/or adjuvant. The kit may further comprise information and/or illustration for the use of the kit.

The present invention also provides a method for the treatment and/or prevention of ischemia comprising administering to a subject a therapeutically effective amount of at least one phospholipase, isoform, derivative, mutant and/or fragment thereof. The phospholipase may be a secretory phospholipase or cytoplasmic phospholipase. The secretory phospholipase may be pancreatic, synovial and/or venomous phospholipase. The phospholipase may be a neutral venom phospholipase. In particular, the phospholipase may be from *Naja* venom. For example, the phospholipase may be from *Naja sputatrix* venom. Even more in particular, the phospholipase may be phospholipase $A_2$. The phospholipase $A_2$. may be selected from any one of Group I to Group XI phospholipase $A_2$.

In particular, there is provided a method for the treatment and/or prevention of ischemia comprising administering to a subject a therapeutically effective amount of phospholipase $A_2$, isoform, derivative, mutant and/or fragment thereof. In particular, the phospholipase, isoform, derivative, mutant and/or fragment thereof, is from snake venom. Even more in particular, the phospholipase $A_2$, isoform, derivative, mutant and/or fragment thereof, is from *Naja* venom. For example, from *Naja sputatrix* venom.

The present invention also provides a method for the treatment and/or prevention of ischemia comprising administering to a subject a therapeutically effective amount of at least one phospholipase, isoform, derivative, mutant and/or fragment thereof, wherein the phospholipase, isoform, derivative, mutant and/or fragment thereof is from *Naja sputatrix* venom.

The phospholipase may be phospholipase $A_2$. The phospholipase $A_2$ may comprise the amino acid sequence of SEQ ID NO:2.

In particular, the phospholipase $A_2$, an isoform, derivative, mutant, and/or fragment thereof comprises an isoform, derivative, mutant, and/or fragment thereof of a polypeptide comprising the amino acid sequence of SEQ ID NO:2.

The phospholipase, isoform, derivative, mutant, and/or fragment comprises at least one amino acid substitution, addition, deletion, and/or at least one chemical modification.

The ischemia according to the method provided according to the invention may be selected from the group consisting of cerebral ischemia, cardiac ischemia, and/or skeletal muscle ischemia. In particular, the ischemia may be cerebral ischemia. The ischemia may also be transient focal ischemia.

Ischemia may be defined as a restriction in blood supply, generally due to an occlusion of a blood vessel, which may be due to an embolus or local thrombosis. Ischemia is a feature of ischemic stroke, heart diseases, transient ischemic attacks, cerebrovascular accidents, ruptured arteriovenous malformations, and peripheral artery occlusive disease.

Ischemia may be further defined as an absolute or relative shortage of the blood supply to an organ. Relative shortage means the mismatch of blood supply (oxygen delivery) and blood request for adequate oxygenation of tissue. In particular, cerebral ischemia may be defined as the absolute or relative shortage of blood supply to the brain, and the tissue may be comprised of neurons. Cardiac ischemia may be defined as the absolute or relative shortage of blood supply to the heart, and the tissue may be comprised of cardiac tissue. Skeletal muscle ischemia may be defined as the absolute or relative shortage of blood supply to the skeletal muscles, and the tissue may be comprised of muscle tissue.

Transient focal ischemia may be defined as the transient and/or temporary reduction in blood flow of one blood vessel. In another aspect, transient multifocal ischemia may be subject to the treatment according to the invention, wherein there is a transient reduction in blood flow of more than one blood vessel.

The method according to the invention may comprise inducing neuroprotective effects in a subject at risk of ischemic stroke. Neuroprotective effects may be described as the blockage of specific mechanisms involved in ischemic cell death, i.e. inhibiting apoptosis. In particular, neuroprotective effects may include intervention to reduce specific mechanisms responsible for neuronal death thereby reducing the brain's intrinsic vulnerability to a given insult.

The subject may be a mammal. In particular, the subject is a human.

The phospholipase, isoform, derivative, mutant and/or fragment thereof, reduces ischemic infarct size compared to tPA and/or MK801. Ischemic infarct may be defined as ischemic infarction. Ischemic infarct may be defined as the region of ischemic tissue that is functionally impaired but viable and potentially salvageable with treatment. In particular, the region of ischemic tissue may be neural tissue. Particularly, the region may be further defined as the penumbra or any region with less severe decline in blood flow which may be defined as the region of tissue that has between 15% to 40% cerebral blood flow during ischemia.

The phospholipase, isoform, derivative, mutant and/or fragment thereof, reduces ischemic cell death compared to tPA and/or MK801. Ischemic cell death may be defined as the total number of cells that undergo apoptosis in the penumbra or any region with less severe decline in blood flow, and may be quantitatively measured as detailed in the examples, with a cytotoxicity assay, the method being well known to a skilled person in the art.

tPA may be defined as tissue plasminogen activator, which induces thrombolysis, in particular tPA dissolves blood clots. MK801 may be defined as dizocilpine, an NMDA (N-methyl-D-aspartate) antagonist.

The present invention also provides a method comprising the administration of at least one phospholipase, isoform, derivative, mutant and/or fragment thereof, to a subject which may result in the reduction of infarct size, decrease in gene expression of thyrotropin releasing hormone, decrease in gene expression of secreted phosphoprotein, decrease in gene expression of moesin, decrease in gene expression of metalloproteinase-9 (MMP-9), decrease in gene expression of tissue inhibitor of matrix metalloproteinase 1 (TIMP-1), decrease in gene expression of calgranulin A, increase in gene expression of glutathione-S-transferase, increase in gene expression of CAM kinase II, and/or increase in gene expression of angiotensinogen compared to the ischemic state. The decrease and increase in gene expression may be obtained through a quantitative real-time PCR analysis as detailed in the examples, the general method being well known to a person skilled in the art.

The method provided may also comprise the administration of phospholipase, isoform, derivative, mutant and/or fragment thereof, wherein at least one anti-apoptotic gene and/or gene transcript may be up-regulated. Particularly, the anti-apoptotic gene may be Bcl-2 and/or Bcl-XL. The method may comprise the administration of phospholipase, isoform, derivative, mutant and/or fragment thereof, in particular, phospholipase $A_2$, isoform, derivative, mutant and/or fragment thereof, wherein at least one pro-apoptotic gene and/or gene transcript may be down-regulated. Particularly, the pro-apoptotic gene may be Bax. The up-regulation and/or down-regulation of anti- and pro-apoptotic genes respectively may be observed by a real-time PCR analysis as detailed in the examples, the general method being well known to a person skilled in the art.

The method to treat and/or prevent ischemia may comprise administering, at least one phospholipase, isoform, derivative, mutant and/or fragment thereof, to a subject:

at least once and/or continuously before the onset of the ischemia;

at least once and/or continuously during the onset of the ischemia; and/or at least once and/or continuously after the onset of the ischemia.

In particular, the phospholipase, isoform, derivative, mutant and/or fragment thereof may be administered at least once and/or continuously before, and/or after the onset of the ischemia; at least once and/or continuously during and/or after the onset of the ischemia; and/or at least once and/or continuously during and/or until 15 minutes after the onset of the ischemia; at least once and/or continuously during and/or until 14 minutes after the onset of the ischemia; at least once and/or continuously during and/or until 10 minutes after the onset of the ischemia.

The phospholipase, isoform, derivative, mutant and/or fragment thereof may be administered at least once and/or continuously during and/or until around 5 minutes after the onset of the ischemia. In particular, the phospholipase, isoform, derivative, mutant and/or fragment thereof may be administered at 0 minutes, at around 1 minute, at around 2 minutes, at around 3 minutes, at around 4 minutes and at around 5 minutes, continuously or at any instant of time in between 0 and around 5 minutes.

The method may also provide the phospholipase, isoform, derivative, mutant and/or fragment thereofto be further administered in combination and/or in succession with at least one a neuroprotective compound different from the phospholipase, isoform, derivative, mutant and/or fragment thereof.

The phospholipase, isoform, derivative, mutant and/or fragment thereof, may be administered in conjunction with at least one pharmaceutically acceptable, excipient, diluent, carrier and/or adjuvant.

The method may be used to treat and/or prevent ischemia in a subject. The subject may be a mammal. The mammal may be a human.

The neuroprotective ability of snake venom NsPLA$_2$ in rat models of focal ischemia has been investigated. However, the present invention is not limited to rat models but encompasses mammalian models.

Our study has shown that a venom phospholipase A$_2$ (NsPLA$_2$) could reduce the focal ischemia caused by occlusion of the left middle cerebral artery by 80%, compared to MK801 (dizocilpine), an NMDA (N-methyl-D-aspartate) antagonist used as a control, which could reduce the infarct size only by 40%. Tissue plasminogen activator (tPA) that is currently in clinical use has been found to be less neuroprotective than the phospholipase A$_2$ described in this invention. We have also observed that the genes that are responsible for ischemic damage are being down regulated when treated with venom phospholipase A$_2$. This is supported by the in vitro studies on organotypic hippocampal culture. NsPLA$_2$ has been found to render neuroprotection in both the OGD (oxygen-glucose deprivation) and glutamate induced cell death and neurotoxicity respectively. This clearly indicates that the natural venom compound, phospholipase A$_2$ is useful in the treatment and/or prevention of ischemia, in particular, cerebral ischemia.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

*N. sputatrix* Venom Fractionation

Figure 1B:
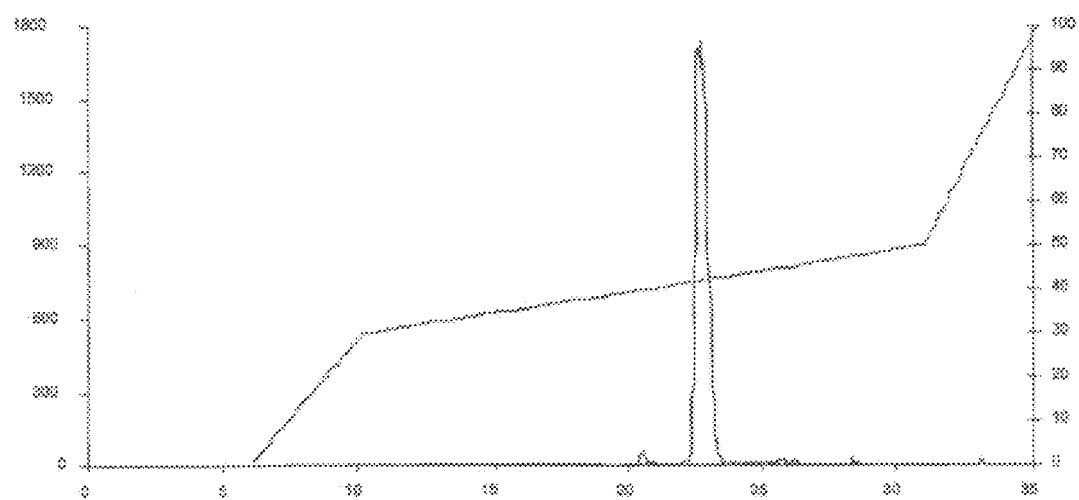
Figure 1C:
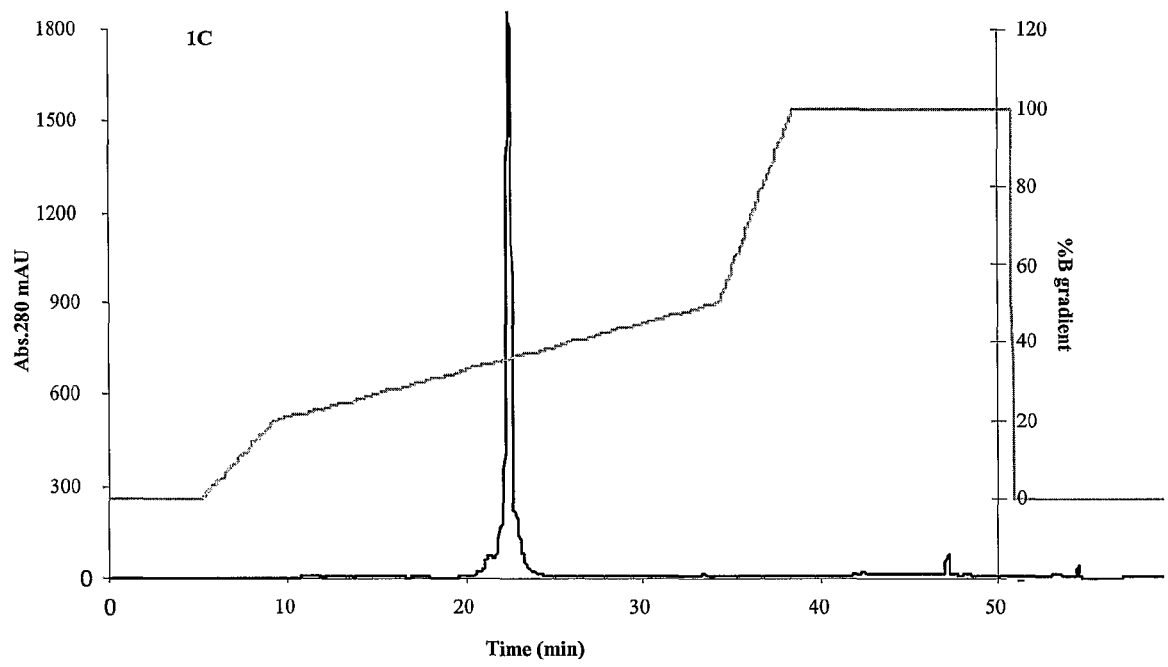

*N. sputatrix* crude venom (Sigma Chemicals, St Louis, USA) was fractionated on Sephadex G-50 gel filtration chromatography using 50 mM Tris-HCl pH8.0. The PLA$_2$ containing protein fractions (Peak 1, FIG. 1A) were pooled and separated further on a reverse-phase High Performance Liquid Chromatography (HPLC) using C18 Jupiter column (FIG. 1B). The partially purified PLA$_2$ protein was fractionated on a second Reversed phase-High Performance Liquid Chromatography (RP-HPLC), using a C4 Jupiter column (FIG. 1C). The buffer system used for the RP-HPLC were buffer A, 0.1% trifluoroacetic acid (TFA) in filtered H$_2$O and buffer B, 0.1% TFA in 75% acetonitrile. All proteins were quantitated using Bradford Assay Reagent (Bio-Rad Laboratories, USA).

cDNA (nucleotide) sequence (SEQ ID NO:1) encoding NsPLA$_2$ precursor (L42005.1)

```
tcacctcgga caaaatgaat cctgctcacc ttctgatcct
ggcagcagtt tgtgtctccc ccttaggagc ctcctctaat
cgtcccatgc ctctcaacct ctatcagttc aaaaacatgg
ttcaatgtac tgtccccaat cgatcttggt ggcattttgc
ggactacggt tgctactgcg gacgcggagg tagcgggaca
ccagtagacg acttggatag gtgctgccag attcatgaca
actgctataa tgaagctgaa aaaatttcca gatgctggcc
ctacttcaag acctattcat acgagtgttc tcaaggcaca
ctcacctgca aaggtggcaa caatgcgtgt gcagctgctg
tctgtgattg tgaccgcttg gcagccatct gcttcgccgg
agccccttac aacgataaca actacaatat cgacctcaag
gcacgttgcc aatgatattt gagaggcta
```

Protein sequence of the NsPLA$_2$ Precursor (Q92085) (SEQ ID NO:3)

```
mnpahllila avcvsplgas snrpmplnly qfknmvqctv
pnrswwhfad ygcycgrggs gtpvddldrc cqihdncyne
aekisrcwpy fktysyecsq gtltckggnn acaaavcdcd
rlaaicfaga pyndnnynid lkarcq
```

The sequence of SEQ ID NO:3 is the sequence of the precursor protein of NsPLA$_2$, which comprises the signal peptide and the mature protein of SEQ ID NO:2.

Mature NsPLA$_2$ Protein Sequence (SEQ ID NO:2)

```
NLYQFKNMVQCTVPNRSWWHFADYGCYCGRGGSGTPVDDLDRCCQIHDNC
YNEAEKISRCWPYFKTYSYECSQGTLTCKGGNNACAAAVCDCDRLAAICF
AGAPYNDNNYNIDLKARCQ
```

Both the nucleotide and protein sequences have been deposited in the NCBI GenBank Database Accession Numbers:
Protein sequence: □92085
Nucleotide sequence: L42005.1, AAA66028.1

Example 2

Figure 2:
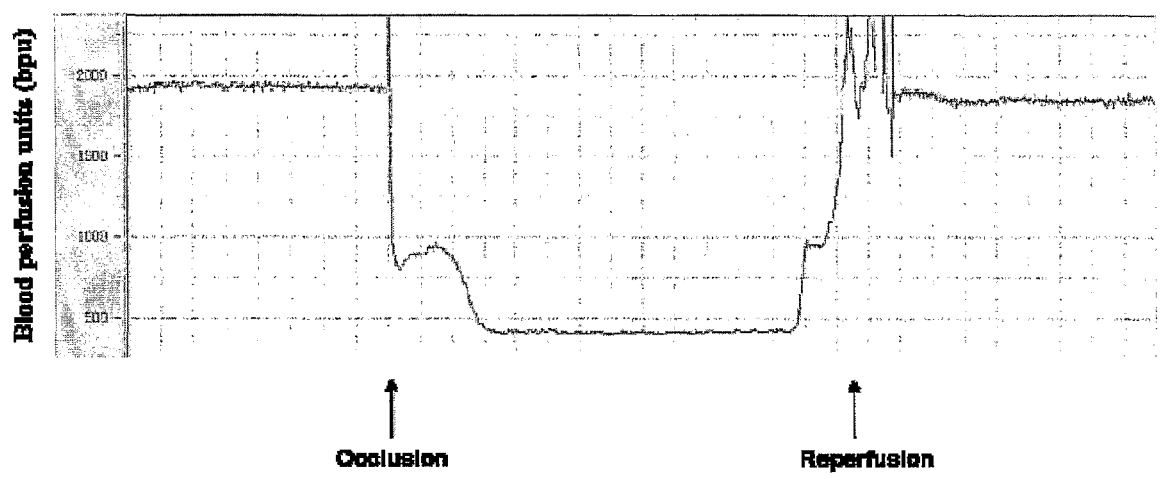

Intravenous Administration of NsPLA$_2$ Confers Protection During Transient Ischemia Transient cerebral focal ischemia was induced by the intraluminal insertion of a nylon suture to occlude the left middle cerebral artery (MCA). The presence of focal occlusion was confirmed using the Laser Doppler that measures the cerebral blood flow in the region of middle cerebral artery (FIG. 2). The ischemic period lasted 60 min, after which the suture was removed and reperfusion initiated. Animals were sacrificed 23 hr later. Phospholipase A$_2$ (PLA$_2$) from *Naja sputatrix* venom, was injected intravenously, at a dose of 30

μg/200 g body weight, immediately-(0 min), 5-, 15-, 30- and 60 min after MCAo (middle cerebral artery occlusion). The amount of NsPLA$_2$ administered is way below its LD$_{50}$ value (125 μg/200 g body weight) and did not induce any signs of toxicity in our studies. Histopathological analysis was carried out to assess the extent of infarction in the brains of rats (FIG. 3A).

Figure 3:
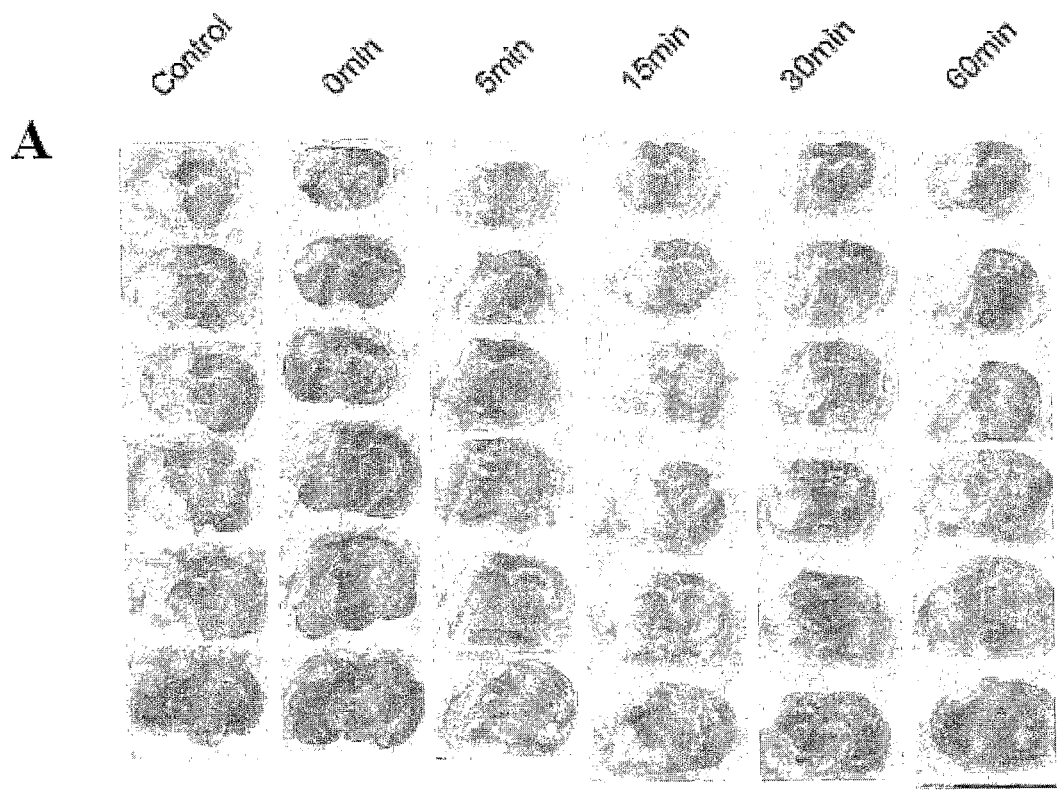
Figure 3:
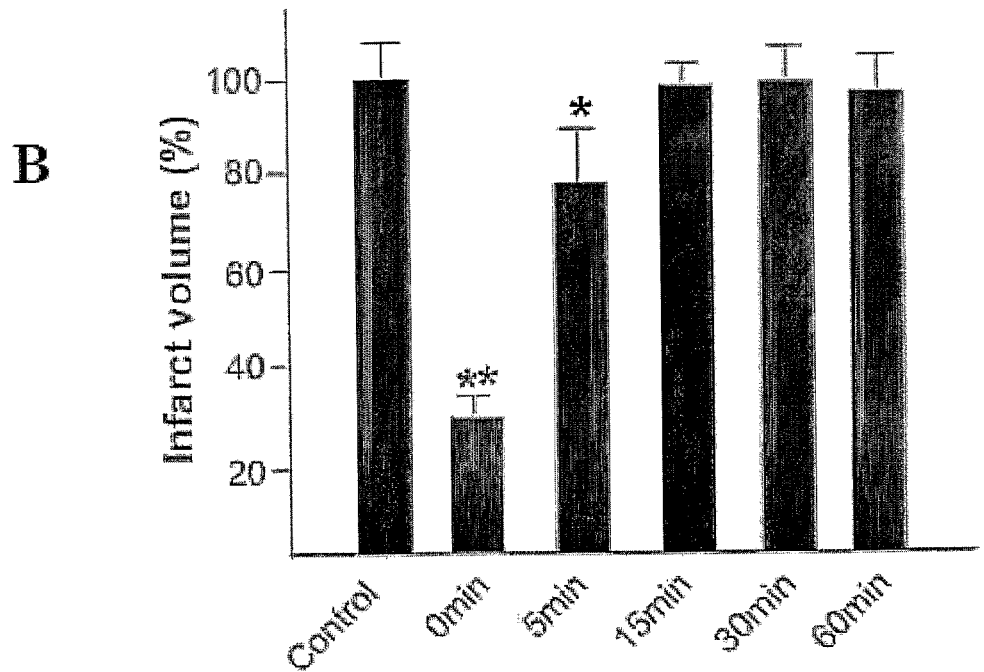
Figure 4A:
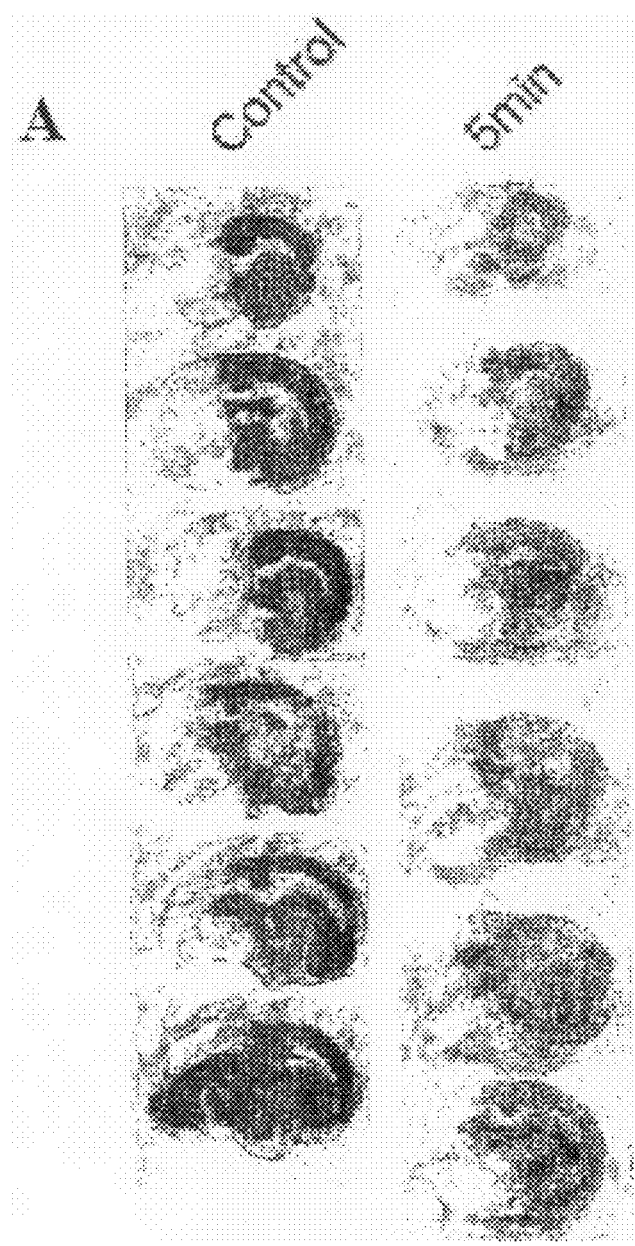
Figure 4B:
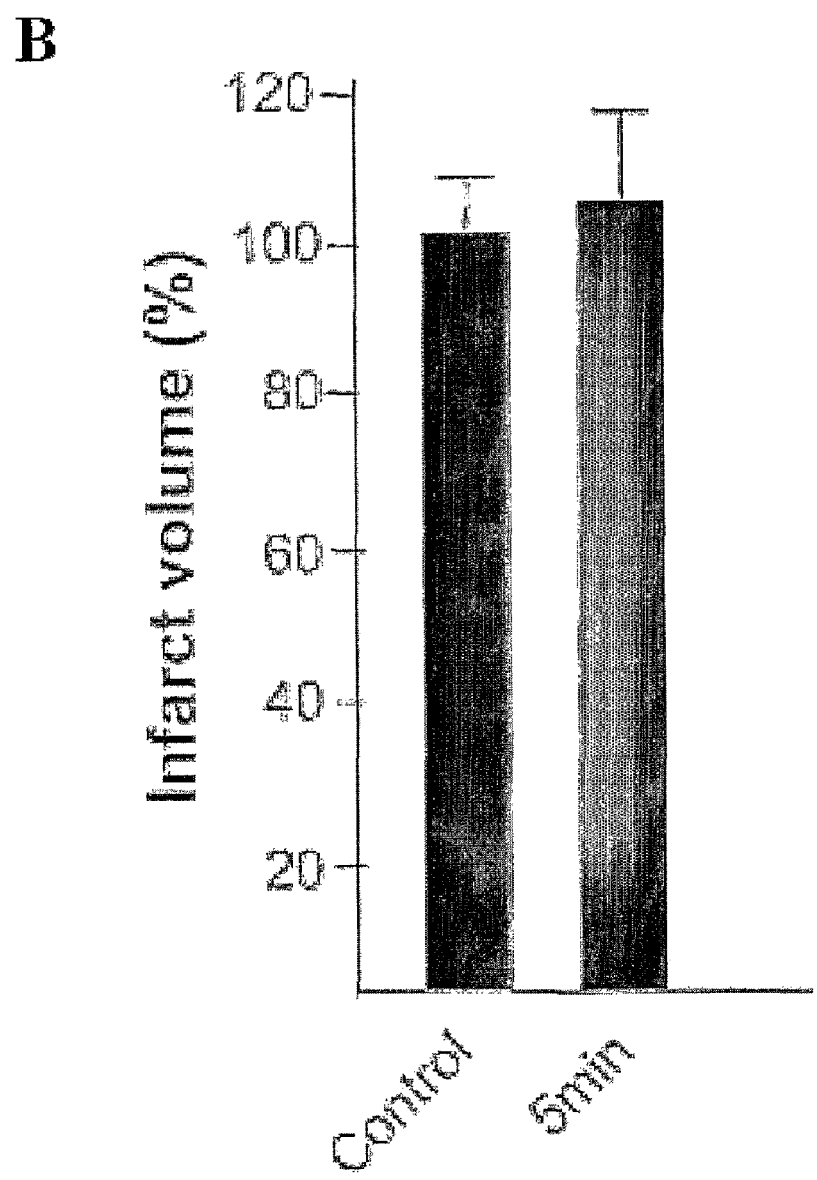

The administration of NsPLA$_2$ immediately post-occlusion resulted in a significant reduction in infarct size, as revealed by TTC (triphenyltetrazolium chloride) staining of serial brain sections. Ischemic damage was markedly attenuated in the striatum and cortex of the brain, although effects were more pronounced in striatal tissue. Administration of NsPLA$_2$ at 5 min post-occlusion (MCAo) also reduced the infarct size but to a lesser extent than 0-min-treatment with NsPLA$_2$. Phospholipase A$_2$, when given 15-, 30- and 60 min post-occlusion and 5 min pre-occlusion had no effect on brain infarction, when compared to the saline-treated control. (FIGS. 3A and 4A).

Quantitative assessment of neuroprotection was carried out by measuring the infarct volume of brain sections (FIG. 3B), that takes into consideration the insult size as well as extent of edema. Intravenous injection of NsPLA$_2$ at 0- and 5 min post-occlusion reduced infarct volume by 66.8% and 21.7% respectively as compared to the saline treated control. In contrast, NsPLA$_2$ administered at 15-, 30- and 60 min post-occlusion did not significantly reduce infarct volumes, relative to the saline-treated control (98.7%±5.6%, 100.5%±7.6% and 97.4%±7.4% and respectively). Treatment with NsPLA$_2$ at 5 min pre-occlusion did not reduce infarct volume significantly either (FIG. 3B, 104.7%±11.7%).

Example 3

MK801, but not tPA, Confers Neuroprotection

The thrombolytic tissue plasminogen activator (tPA) is a serine protease that initiates the process of clot degradation by converting plasminogen to activated plasmin. Animal experiments had demonstrated that tPA improved functional outcomes and reduced infarct volumes (Zivin et al, 1985; 1988). The National Institute of Neurological Disorders and Stroke study (The National Institute of Neurological Disorders and Stroke rtPA Stroke Study Group, 1995) established that acute administration of tPA significantly reduced the incidence of long-term disability despite a slight increase on the risk of intracerebral hemorrhage, leading to its approval by the Food and Drug Administration for the treatment of acute ischemic stroke. Dizocilpine, or MK801, is a non-competitive antagonist of the NMDA receptor and has been shown in several animal studies to confer neuroprotection by inhibiting glutamate-induced excitotoxicity (Buchan et al, 1992; Yang et al, 1994; Bertorelli et al, 1998).

Figure 5A:
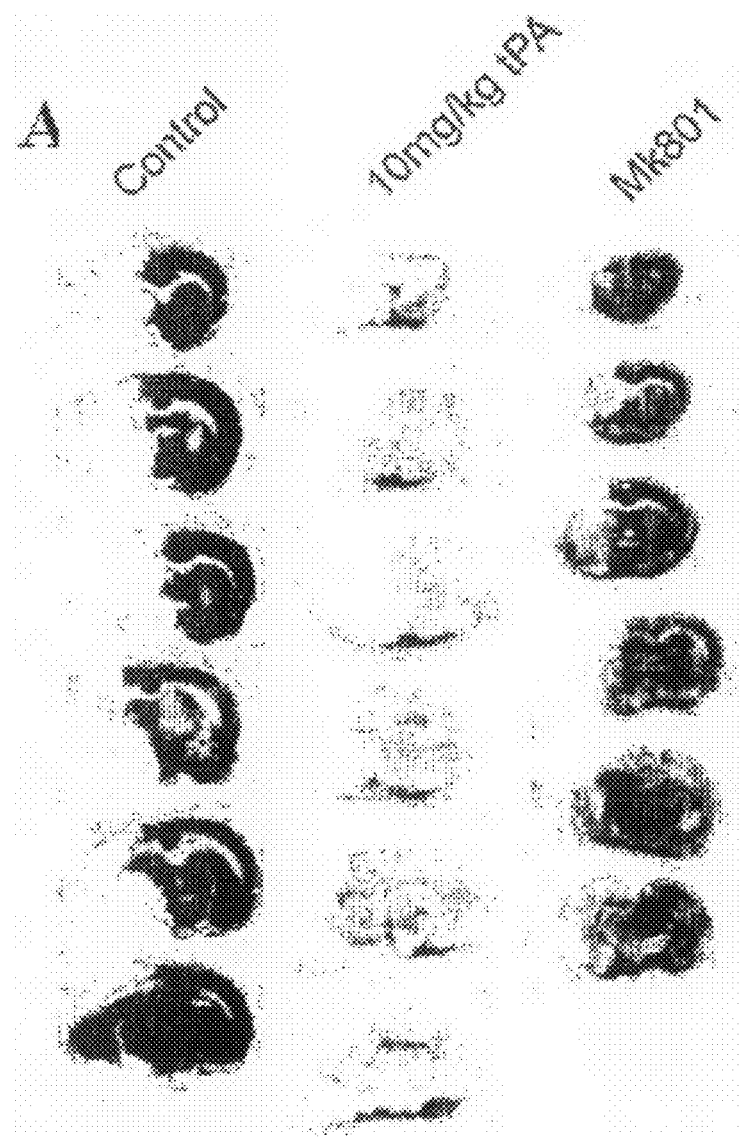
Figure 5B:
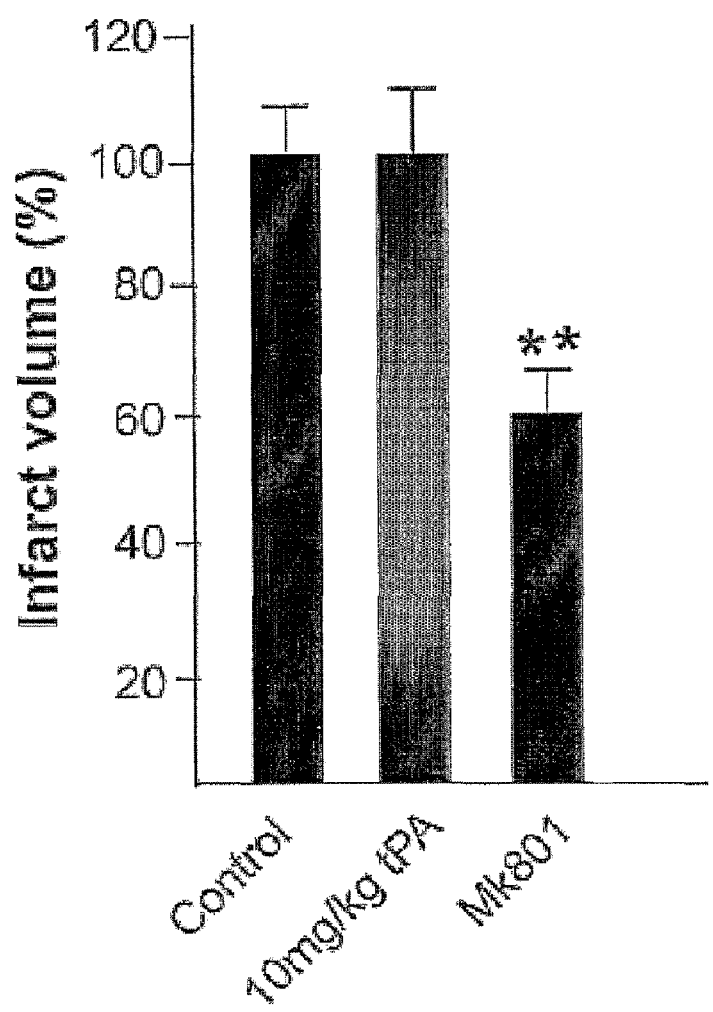

Both tPA (tissue plasminogen activator) and MK801 (dizocilpine) were used in the treatment of ischemia and their efficacies in reducing infarct volume were compared to that of NsPLA$_2$. Infusion of 10 mg/kg body weight tPA over a period of 1 hr, starting 30 min post-occlusion, did not significantly reduce infarct volume after transient ischemia (FIG. 5). Although this dose is well above that usually applied to humans (0.9 mg/kg body weight), it much better reflects the pathophysiological situation because the thrombolytic activity of tPA is approximately 10-fold lower in rodents than in human patients. Hence, a dose of 10 mg/kg body weight is almost equivalent to the dose of 0.9 mg/kg body weight in humans (Kilic et al, 2001). An infusion regimen was also necessary due to the short half-life of tPA in the blood. On the other hand, the administration of MK801 in three doses, 2.5 mg/kg body 30 min prior to MCAo followed by 1.25 mg/kg body weight 6 hr and 14 hr post-occlusion, significantly reduced infarct volume as compared to the saline treated control (FIG. 5; 61.1%±8.6%, p<0.01). The extent of neuroprotection conferred by MK801 was less than that by NsPLA$_2$ when administered immediately post-occlusion (33.2%±5.1%) but greater than that conferred by NsPLA$_2$ treatment 5 min after MCAo (78.3%±10.8%; FIG. 5).

Example 4

Administration of NsPLA$_2$ Protects Neurons from Ischemic Cell Death

Neurons within the ischemic core die exclusively by means of a necrotic mechanism as a result of the excitotoxcity cascade triggered by energy depletion. Damage within the penumbra, on the other hand, is mediated by different mechanisms. As the ATP levels and blood flow are only marginally reduced within the penumbra, there is insufficient ischemia to directly cause the cataclysmic processes that happen so quickly with the core (Smith, 2004). Sublethal injury to neurons favours the initiation of apoptosis, causing penumbral neurons to die by means of this pathway rather than by necrosis, depending on the magnitude of initial injury.

Figure 6A:
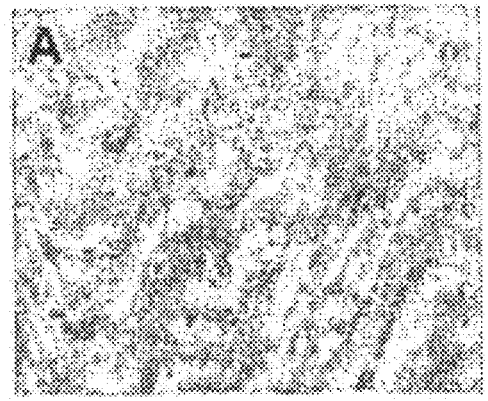
Figure 6B:
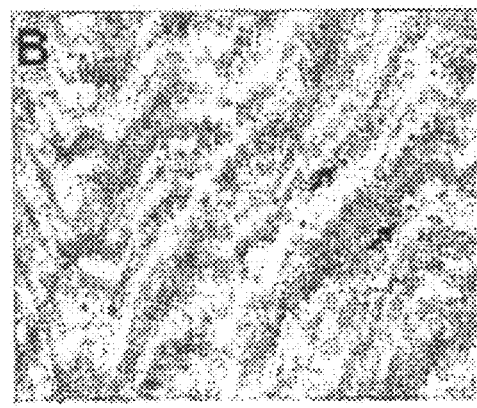
Figure 6C:
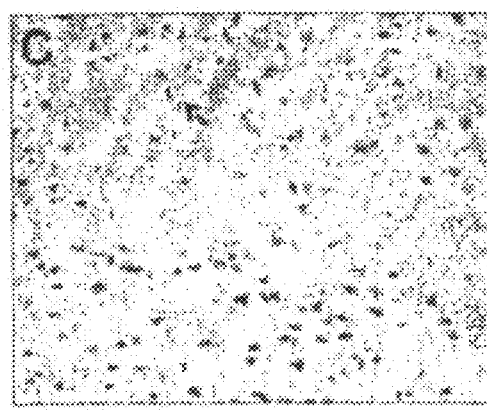
Figure 6D:
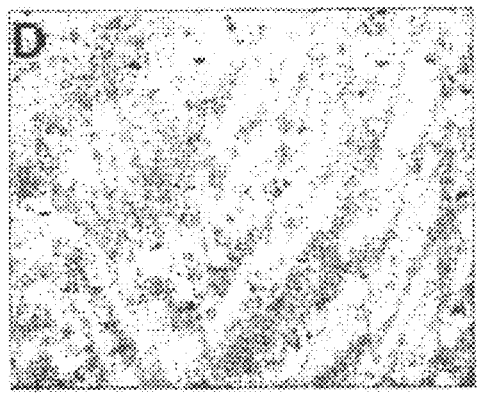
Figure 6E:
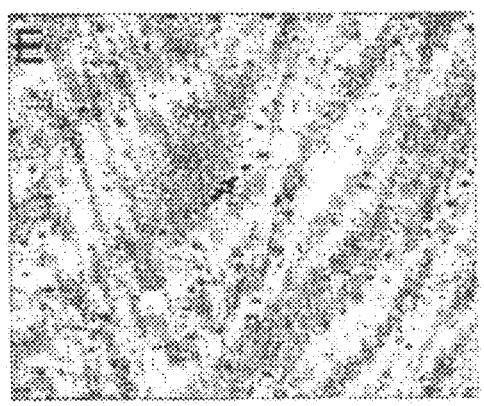
Figure 6F:
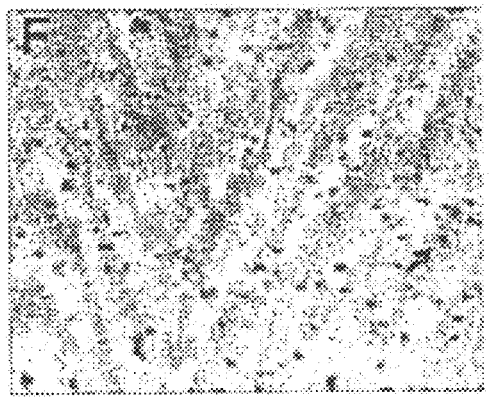

The ability of NsPLA$_2$ to protect neurons from cell death was investigated. Paraffin-embedded rat brains were sectioned and stained with haematoxylin and eosin. Cellular morphology was evaluated using light microscopy, which revealed extensive tissue damage and edema in the striatum and cortex of ischemic brains (FIGS. 6B and E). Neurons appeared shrunken and nuclei were dysmorphic and pyknotic. Administration of NsPLA$_2$ at 0 min post-occlusion significantly reduced ischemic damage (FIGS. 6C and F). Tissue integrity was retained and edema was greatly reduced. In addition, many cell nuclei exhibited normal morphology.

Figure 7A:
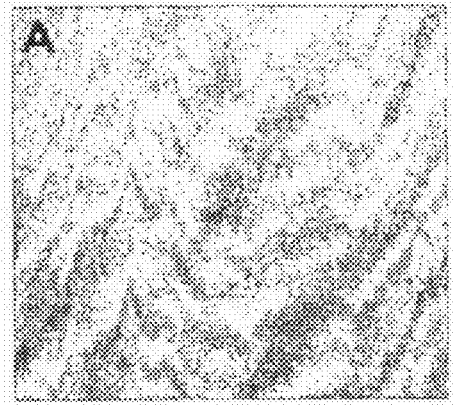
Figure 7B:
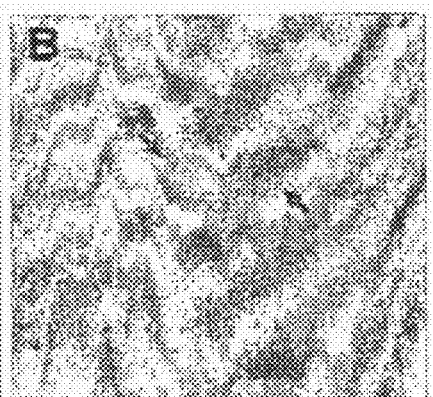
Figure 7C:
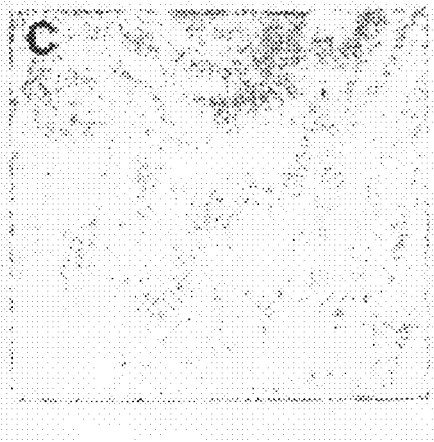
Figure 7D:
Figure 7E:
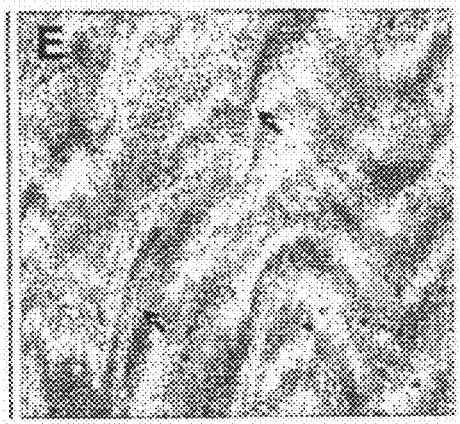
Figure 7F:

Subsequently, the TUNEL assay was carried out to assess the extent of apoptosis in ischemic brains. The assay distinguishes apoptosis from necrosis by specifically detecting DNA cleavage and chromatin condensation, hallmarks of apoptotic cell death. Free 3'-OH termini of fragmented DNA are enzymatically labelled with modified nucleotides and detected immunohistochemically. Brain sections were stained and normal, control cells appeared green (FIGS. 7A and D). In contrast, almost all the neurons in the striatum and cortex of ischemic brains were apoptotic (FIGS. 7B and E) and their nuclei were stained brown. The degree of apoptosis was greatly reduced by the administration of PLA$_2$ immediately post-occlusion, as evidenced by the reduction in number of apoptotic cells. DNA integrity was almost completely preserved. The cortical neurons appear to be less protected from ischemic insult than striatal neurons (FIGS. 7C and F). This is in concordance with the observations described in section 6.2, where TTC (triphenyltetrazolium chloride) staining was restored to a greater extent in the striatum than in the cortex by NsPLA$_2$. Taken together, these results demonstrate the ability of NsPLA$_2$ to protect neurons in the penumbra from ischemic damage.

Example 5

Neuroprotective Activity of Phospholipase A$_2$

Figure 9:
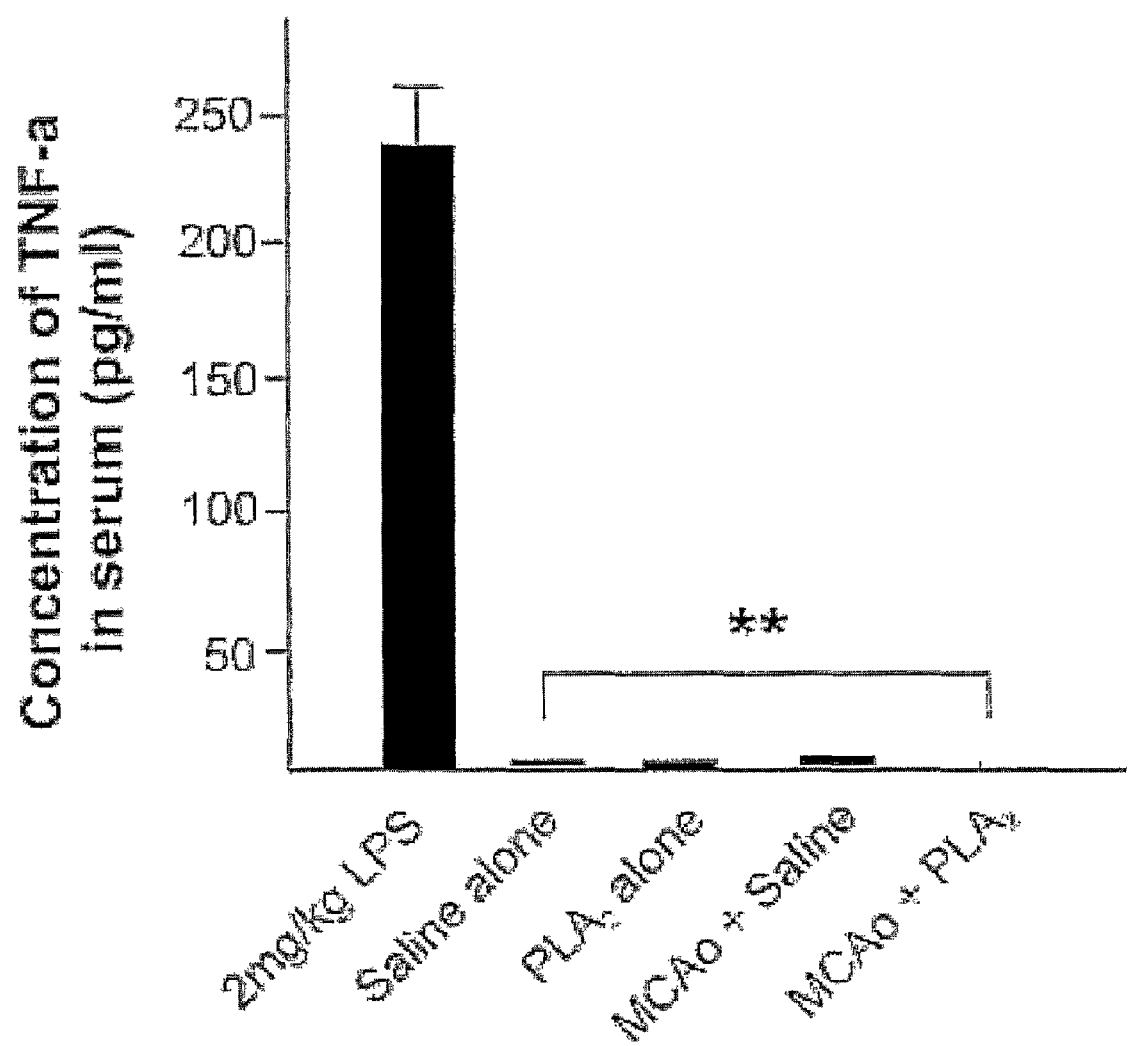

Our invention describes an important and novel neuroprotective property to snake venom PLA$_2$. To the best of our knowledge, this is the first report on the therapeutic potential of NsPLA$_2$ in the treatment of stroke. Phospholipase A$_2$ from the venom of *N. sputatrix* significantly reduced the infarct volume when administered at a sub-lethal dose immediately- and 5 min post-occlusion (FIG. 3). Furthermore, NsPLA$_2$ treatment dramatically protected neurons from ischemic cell death (FIGS. 6 and 7). This protection was very pronounced in the striatum, one of the areas most susceptible to energy deprivation and ischemic insult (Pisani et al, 2004). In addition, NsPLA$_2$ conferred a greater extent of neuroprotection as compared to MK801, a known NMDA antagonist, and the dosage required for its protective effect did not induce systemic inflammation (FIG. 9). These observations serve to highlight the potential of NsPLA$_2$ to act as a neuroprotective agent.

Example 6

Gene Expression Analysis of Ischemia and NsPLA$_2$-Induced Neuroprotection

Cerebral ischemia is a powerful stimulus for the de novo expression of many gene systems and identification of genes differentially expressed in the ischemic and non-ischemic brain can help illuminate pathophysiology and provide therapeutic targets in ischemia. Analysis of gene expression can also aid in elucidating the role of various pathways or specific genes in the mechanism of action of neuroprotective agents. Consequently, the power of high-density oligonucleotide arrays was harnessed to generate global expression profiles of non-ischemic, ischemic and NsPLA$_2$-treated brains. RNA isolated from the brains of sham-operated rats (sham-op; n=4), rats subjected to 60 min of MCAo (MCAo; n=4) and rats subjected to 60 min of MCAo but treated with 30 μg/200 g body weight NsPLA$_2$ immediately post-occlusion (MCAo+ NsPLA$_2$; n=4) was pooled before microarray probe preparation and hybridization to minimize inter-individual variation. Expression analysis was carried out using GeneChips from the RAE-230A Array set, with each chip representing ~15,900 genes and expressed sequence tags (ESTs). Genes whose expression changed by 1.7-fold or greater in at least one pairwise comparison (between sham-op and MCAo or between MCAo and MCAo+NsPLA$_2$) were deemed significant.

In an attempt to understand the mechanisms by which NsPLA$_2$ may confer neuroprotection, the gene expression profiles of MCAo and MCAo+NsPLA$_2$ were compared. Amongst the 205 genes found to be differentially regulated, 43 were of particular interest as they had also been observed to be differentially expressed in the sham-op-MCAo comparison. They are listed in Table 1 and include genes involved in cell growth and maintenance (retinol-binding protein, regulator of G-protein signalling 2, DNA topoisomerase, X transporter protein 3, hemoglobin &chain complex, nucleosome assembly protein 1-like, cyclin-dependent kinase inhibitor 1A and chloride intracellular channel 4), development (tropomyosin 4 and neurogenic differentiation 1), lipid metabolism (tissue inhibitor of metalloproteinase 1 and sulfotransferase family 1A), Ca$^2$+-binding (calpactin 1 heavy chain, calgranulin A, protein disulfide isomeraserelated protein and S-100 related protein), maintenance of cytoskeletal structure (tropomyosin 1 and moesin), defense response (CD44 antigen), regulation of blood pressure (angiotensinogen), cell-cell signaling (thyrotropin releasing hormone), antioxidant activity (glutathione-S-transferase), proteolysis (MMP-9), cell adhesion (l-gicerin) and transcriptional regulation (POU domain). Most of these genes have been down-regulated by PLA$_2$, even as their expression was increased by ischemia, and may play important roles in its neuroprotective activity.

TABLE 1

List of genes whose expression was changed by NsPLA$_2$ treatment when compared to saline-treated MCAo (middle cerebral artery occlusion) controls

| Gene ID | | Description |
|---|---|---|
| 1369421_at | −4.6 | DNA topoisomerase I |
| 1370792_at | −4.3 | microtubule-associated protein, RP/EB family, member 1 |
| 1387952_a_at | −3.7 | CD44 antigen |
| 1368912_at | −3.5 | thyrotropin releasing hormone |
| 1387391_at | −3 | cyclin-dependent kinase inhibitor 1A |
| 1370902_at | −2.6 | aldose reductase-like protein |
| 1371499_at | −2.6 | CD9 antigen |
| 1368144_at | −2.44 | regulator of G-protein signaling protein 2 |
| 1370288_a_at | −2.44 | tropomyosin 1, alpha |
| 1370997_at | −2.44 | homer, neuronal immediate early gene, 1 |
| 1368948_at | −2.3 | moesin |
| 1373473_a_at | −2.3 | nucleosome assembly protein 1-like 1 |
| 1368838_at | −2.1 | tropomyosin 4 |
| 1388331_at | −2.1 | tumor rejection antigen gp96 |
| 1367712_at | −2 | tissue inhibitor of metalloproteinase 1 |
| 1369166_at | −2 | matrix metalloproteinase 9 |
| 1370007_at | −2 | protein disulfide isomerase related protein (calcium-binding protein) |
| 1367849_at | −1.9 | syndecan 1 |
| 1370575_a_at | −1.9 | ornithine decarboxylase antizyme inhibitor |
| 1371310_s_at | −1.9 | serine (or cysteine) proteinase inhibitor, clade H, member 1 |
| 1375170_at | −1.9 | Similar to endothelial monocyte-activating polypeptide |
| 1386890_at | −1.9 | S-100 related protein |
| 1387420_at | −1.9 | Chloride intracellular channel 4 |
| 1367584_at | −1.75 | calpactin I heavy chain |
| 1367939_at | −1.75 | retinol binding protein 1 |
| 1368494_at | −1.75 | S100 calcium-binding protein A8 (calgranulin A) |
| 1369705_at | −1.75 | X transporter protein 3 |
| 1369793_a_at | −1.75 | I-gicerin |
| 1371102_x_at | −1.75 | hemoglobin beta chain complex |
| 1372500_at | −1.75 | Similar to tropomodulin 3 |
| 1389533_at | −1.75 | fibulin 2 |
| 1390383_at | −1.75 | Adipose differentiation-related protein |
| 1369993_at | 1.74 | Calcium/calmodulin-dependent protein kinase (CaM kinase) II gamma |
| 1373057_at | 1.74 | ProSAPiP1 protein |
| 1387288_at | 1.74 | neurogenic differentiation 1 |
| 1368577_at | 1.87 | gap junction protein, beta 6 (connexin 30) |
| 1370019_at | 1.87 | sulfotransferase family 1A, phenol-preferring, member 1 |
| 1376734_at | 1.87 | NOV protein |
| 1387811_at | 1.87 | angiotensinogen |
| 1367774_at | 2 | glutathione S-transferase, alpha 1 |
| 1374444_at | 2 | Similar to plexinB1 |
| 1370432_at | 13.93 | POU domain, class 3, transcription factor 1 |

Real-Time Quantitation of Gene Expression

Figure 8A:
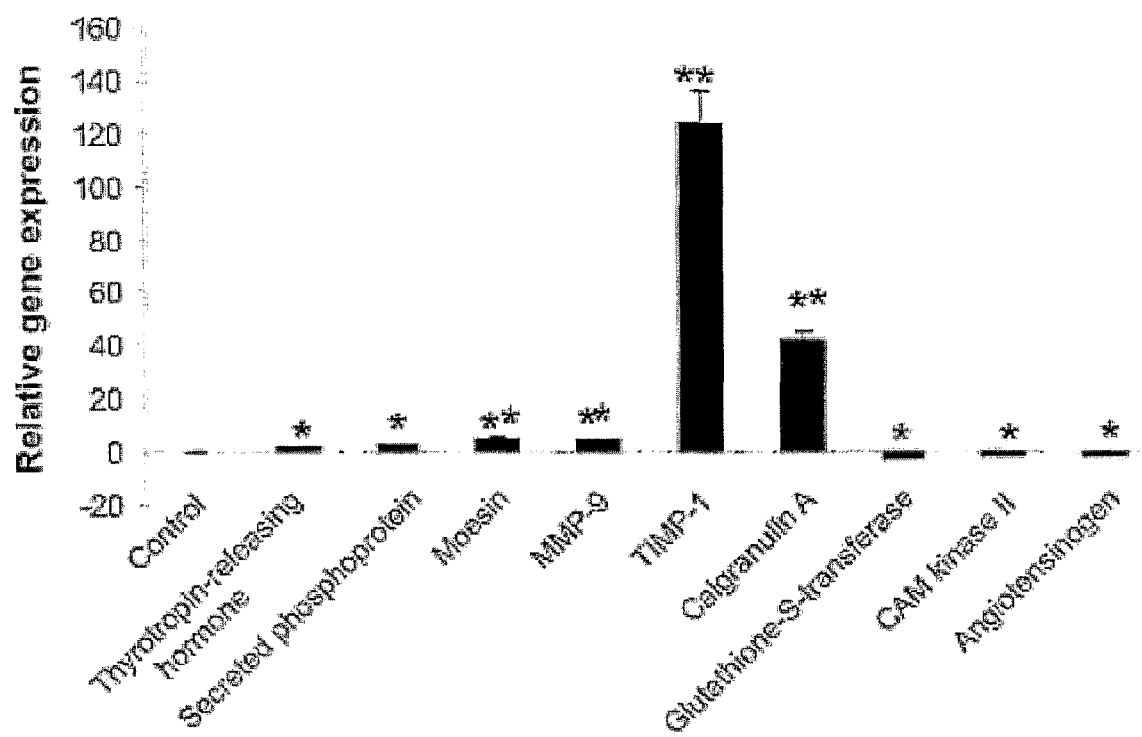
Figure 8B:
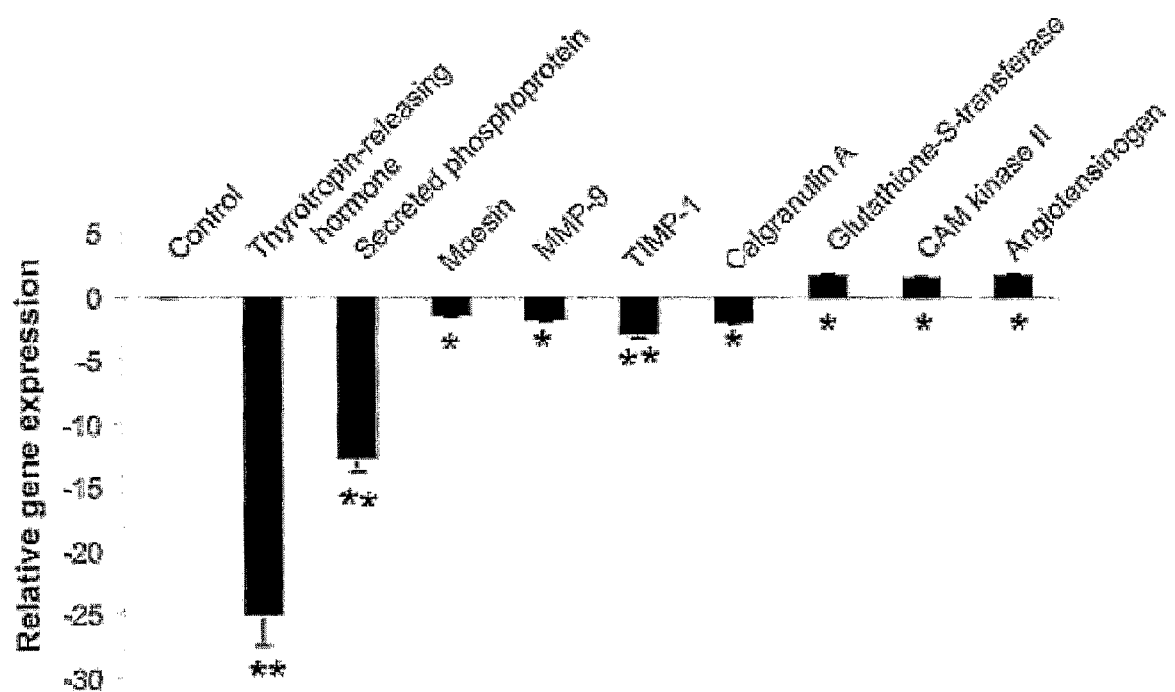

The expression of nine genes that may have important roles in mediating the neuroprotective action of NsPLA$_2$ was quantitated by real-time PCR (FIG. 8). Specific primers were used for PCR amplification. The relative expression of each gene in the heart was obtained after normalizing against an internal control (18S ribosomal RNA) and a calibrator, in this case, the sham-operated control or MCAo brain, FIGS. 8A and B respectively, relative gene expression=1). Thyrotropin releasing hormone, secreted phosphoprotein, moesin, MMP-9, tissue inhibitor of matrix metalloproteinase 1 (TIMP-1) and calgranulin A were all upregulated during cerebral ischemia whilst glutathione-S-transferase, CAM kinase II and angiotensinogen were down-regulated (FIG. 8A). The same genes showed decreased and increased expressions respectively in response to NsPLA$_2$ treatment (FIG. 8B). Hence, the gene expression changes quantified by realtime PCR correlated well with the microarray data (Table 1). Due to the different specificities and sensitivities of the two technologies, the absolute values for fold-change did not necessarily correspond. However, the expression profiles obtained in both cases proved to be similar, thereby validating the results of microarray analysis.

Gene Expression Analysis of Focal Ischemia and Phospholipase $A_2$-Mediated Neuroprotection In order to understand some of the mechanisms underlying NsPLA$_2$-mediated neuroprotection, global gene expression analysis was carried out on sham-operated, ischemic and NsPLA$_2$-treated brains. An initial comparison of the expression profiles from sham-operated and ischemic brains provided a molecular fingerprint of the genomic responses elicited by transient focal ischemia. Focal stroke initiates a cascade of new gene expression, which is evidenced here by the large number of up-regulated transcripts (148 out of 205 differentially regulated genes). The pattern of change is usually exhibited as 'waves' of sequential genes expressed over a period of time. Transcription factors (immediate early genes) typically comprise the first wave as shown by members of the fos and jun families that are rapidly and transiently up-regulated (Uemura et al, 1991; Hsu et al, 1993). A second wave consists of the heat shock proteins whose mRNA is expressed within 1 to 2 hr followed by a gradual decline in 1 to 2 days (Nowak et al, 1990). The third wave (1 to 2 days) was initially characterized by the initiation of the inflammatory gene expression cascade but has now been expanded to include neurotrophic factors and cell death mediators. Genes induced in the inflammatory cascade include TNF-a (Liu et al, 1994), IL-1β (Liu et al, 1993), IL-6 (Wang et al, 1995a), IL-8 and monocyte chemoattractant protein-1 (Wang et al, 1995b). A fourth wave (2-3 days) of new gene expression may be associated with the acute inflammatory reaction to ischemia and comprises proteolytic enzymes (eg. metalloproteinases) implicated in damage to the extracellular matrix (Rosenberg et al, 1996), as well as their endogenous protease inhibitors. The final wave (more than 3 days) includes mediators such as transforming growth factor-β (TGF-β) and secreted phosphoprotein 1, which may be important in tissue remodeling.

A comparison of the gene expression profiles from ischemic and NsPLA$_2$-treated brains revealed forty-three genes (Table 1) that are differentially regulated. Intriguingly, genes upregulated by ischemia were downregulated by NsPLA$_2$ and vice versa. Although the direction of change in the expression of most transcripts may not have been altered when compared to sham-operated brains, significant changes brought about by treatment suggest that these genes may be important in NsPLA$_2$-mediated neuroprotection.

MMP-9, tissue inhibitor of metalloproteinase-1 (TIMP-1) and secreted phosphoprotein-1 are key proponents of the ischemic process and their expression is induced after focal stroke (Wang et al, 1998a, b; Ellison et al, 1998; Fujimura et al, 1999). Matrix metalloproteinases are a family of zinc-binding proteolytic enzymes capable of degrading components of the extracellular matrix. MMP-9 is able to digest the endothelial basal lamina, which plays a major role in maintaining BBB impermeability. The BBB serves to protect the central nervous system from invasive agents such as inflammatory cells and bacteria, as well as chemical agents. Damage to BBB often results in edema and subsequent neuronal cell death (Rosenberg, 1995). During ischemia, degradation of the basal lamina is reported to occur as early as two hours after insult (Hamann et al, 1995), resulting in BBB permeability soon after. The induction of TIMP-1 expression during ischemia and its concomitant downregulation after NsPLA$_2$ treatment suggest its role in the attenuation of MMP-9 action. Secreted phosphoprotein-1 is a matrix protein expressed during wound healing and may be important in glial scar formation after focal stroke (Ellison et al, 1998) whilst fibulin 2 belongs to a family of matrix proteins that are associated with elastic fibres and basement membranes (Argraves et al, 2003). Both genes are downregulated after NsPLA$_2$ treatment. Taken together, it appears that NsPLA$_2$ administration may have reduced BBB permeability and neuronal injury. Consequently, a lesser extent of matrix remodeling was necessary.

Calgranulin A is synthesized by activated astrocytes and microglial and participates in inflammatory responses within the peri-infarct area, resulting in infarct expansion (Beschomer et al, 2000; Matsui et al, 2002). Similarly, syndecan-1 and CD44 are expressed by macrophages and participate in cytokine gene expression (Li et al, 1997; Wang et al, 2001) whilst gp96 elicits CD4+ T cell cytokine production (Baker-LePain et al, 2004). Their simultaneous down-regulation suggests an attenuated inflammatory assault on the ischemic brain. A recent study by Wang and colleagues (2002) demonstrated that CD44-deficient mice exhibited reduced infarct volume and improved neurological function after transient focal ischemia. In addition, this protection was associated with normal physiological parameters, cytokine gene expression, astrocyte and microglial activation as compared to wild-type mice.

Inhibition of thyrotropin releasing hormone, whose expression was decreased by 3.5-fold after PLA$_2$ treatment, was shown to protect the brain from ischemic insult (Read et al, 2001). Somewhat surprisingly, the expression of moesin was downregulated by PLA$_2$. Since moesin is involved in the modulation of neurite growth cone formation and promotion of cell survival (Paglini et al, 1998), its induction by PLA$_2$ would be expected to contribute to neuroprotection. However, the expression of moesin was shown to be upregulated by focal ischemia (MacManus et al, 2004), probably as part of the arsenal of endogenous protective mechanisms. Hence, a decreased expression here may again demonstrate that neuronal injury was reduced by NsPLA$_2$.

Reactive oxygen species are produced during reperfusion and have been implicated in BBB disruption and infarct expansion after transient focal ischemia. Hence, antioxidant enzymes, such as superoxide dismutase-1, have been demonstrated to play a protective role (Kinouchi et al, 1991; Kondo et al, 1997). Based on this, the increase in expression of glutathione-S-transferase (+2.0-fold) after PLA$_2$ administration may be important in ameliorating oxidative stress-induced neuronal death. However, reperfusion injury is not expected to contribute significantly to ischemic damage here since reperfusion was initiated after just one hour of ischemia. Reperfusion at a later period would exacerbate ischemic damage (Nagahiro et al, 1998). An increase in CAM kinase II transcript is also expected to exert a beneficial effect during stroke since both the expression and activity of this protein are decreased in the CA1 region of the hippocampus after transient focal ischemia (Nagahiro et al, 1998). An imbalance of CAM kinase II-dependent protein phosphorylation-dephosphorylation was hypothesized to be involved in neuronal death. The most dramatic increase in expression was seen in POU-domain transcription factor-1 (+13.9-fold). This transcription factor is expressed by promyelinating Schwann cells in vivo and oligodendrocyte progenitors in vitro. It is also highly expressed during myelination of regenerating axons following toxin-induced demyelination or crush injury in the adult (Sim et al, 2002). Hence, the expression of transcription factor 1 here may be indicative of NsPLA$_2$-induced neuronal regeneration after ischemic damage. The role of angiotensinogen in the neuroprotective activity of NsPLA$_2$ is unclear since its cleavage product, angiotensin II, is a potent vasoconstrictor which has been defined as a significant contributor to the pathophysiology of ischemic stroke (Walther et al, 2002). An assessment of the functional roles of genes listed in Table 1 provides a molecular picture of neuronal tissue that had been damaged to a lesser extent, as a result of NsPLA$_2$ administration, in ischemia.

Furthermore, apart from showing neuroprotection in the in vivo MCAo (middle cerebral artery occlusion) rat model, neuroprotection is also observed in in vitro system. Neurotoxicity induced by glutamate in the organotypic hippocampal slice culture was protected by NsPLA$_2$. This protection was also observed when the culture was incubated in oxygen-glucose deprived conditions (mimicking the in vivo ischemia). In both cases, the NsPLA$_2$ protected the damage in a dose dependent manner and both the CA1 and the CA2/3 region of the hippocampal tissue were protected.

Example 7

Study of NsPLA$_2$ on Systemic Inflammation

Snake venom NsPLA$_2$ has been shown to induce inflammation and this is an issue of concern in its use as a neuroprotective agent. To ascertain if NsPLA$_2$, administered intravenously at a low dose of 30 μg/200 g body weight here, causes systemic inflammation, blood plasma TNF-a levels were measured. Tumour necrosis factor-a is a cytokine secreted by activated macrophages, monocytes, T cells, neutrophils and natural killer cells. Tumour necrosis factor-a is widely acknowledged to be an important inflammatory mediator and its detection in body fluids has been routinely used as a marker of inflammation during disease pathogenesis (Blake and Ridker, 2001; McKay et al, 2001).

Adult male Sprague-Dawley rats (n=6) were administered either saline or NsPLA$_2$ (30 μg/200 g body weight) intravenously. Since cerebral ischemia triggers the inflammatory response and may augment the effects of NsPLA$_2$ in the blood, rats were also subjected to MCAo before saline or NsNsPLA$_2$ treatment (n=6). In addition, rats injected intraperitoneally with bacterial lipopolysaccharide (LPS) served as a positive control for TNF-a induction (Izeboud et al, 2004). Whole blood was withdrawn after 1 hr in heparin-coated syringes and plasma was obtained by centrifugation. Tumour necrosis factor-a levels were subsequently measured by ELISA and the results are shown in FIG. 9. Bacterial LPS dramatically increased plasma TNF-a levels (232±25.1 pg/ml) as compared to the saline-treated control (2.6±0.05 pg/ml). In contrast, NsPLA$_2$ failed to induce significant TNF-a release or expression in both normal and ischemic rats (4.1±0.03 pg/ml and 1.0±0.01 pg/ml respectively) and really reflect basal circulating levels in the blood. Preliminary studies (results not shown) had demonstrated that plasma TNF-a levels peaked 1 hr after LPS administration, followed by a gradual decline over time. Hence, this time-frame was deemed suitable for the experiment conducted here. It is clear, then, that NsPLA$_2$, when administered at low dose, is unlikely to cause systemic inflammation even under ischemic conditions.

Example 8

NsPLA$_2$ Protects Organotypic Hippocampal Cells from Glutamate Insult

Figure 10A:
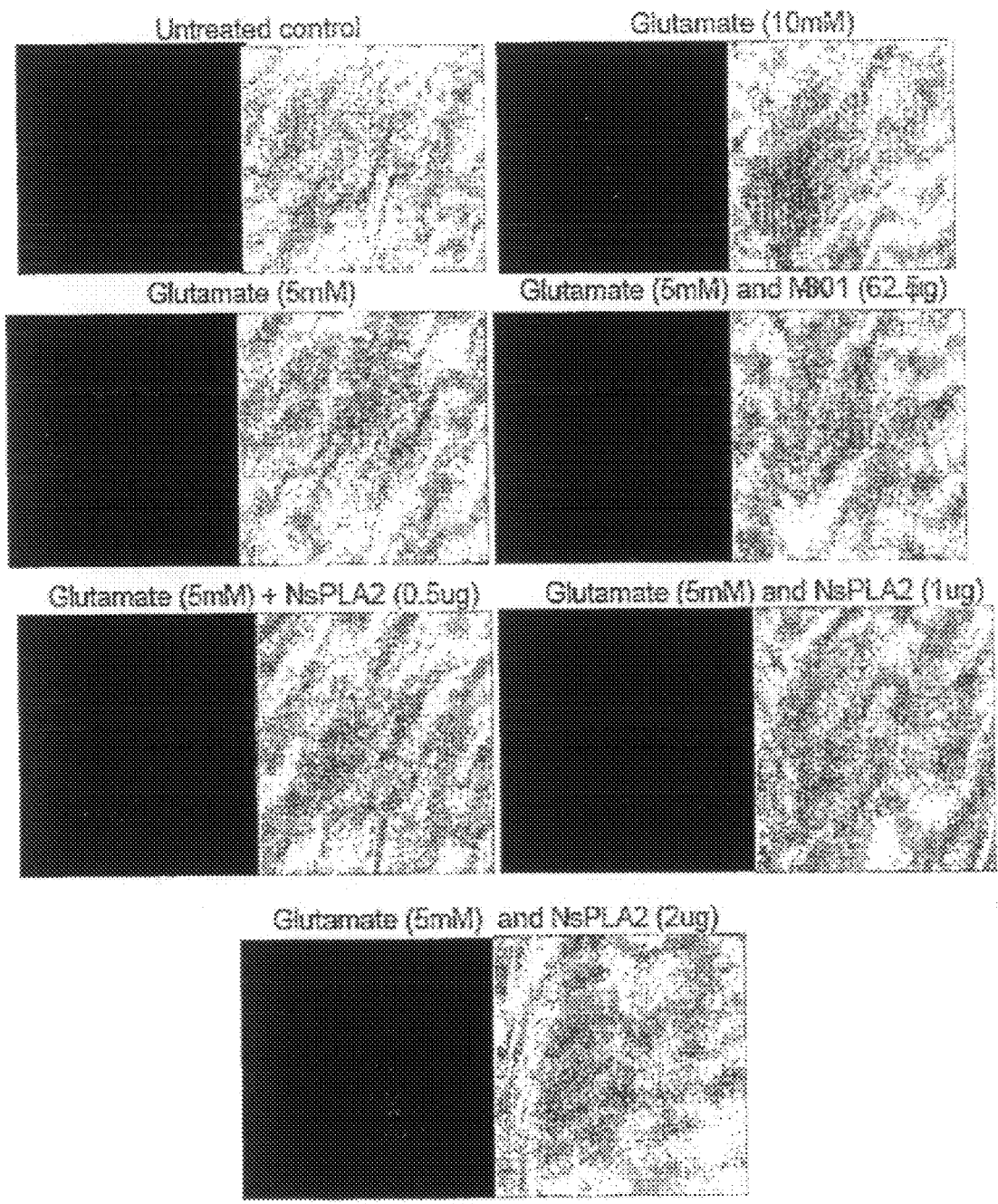
Figure 10C:
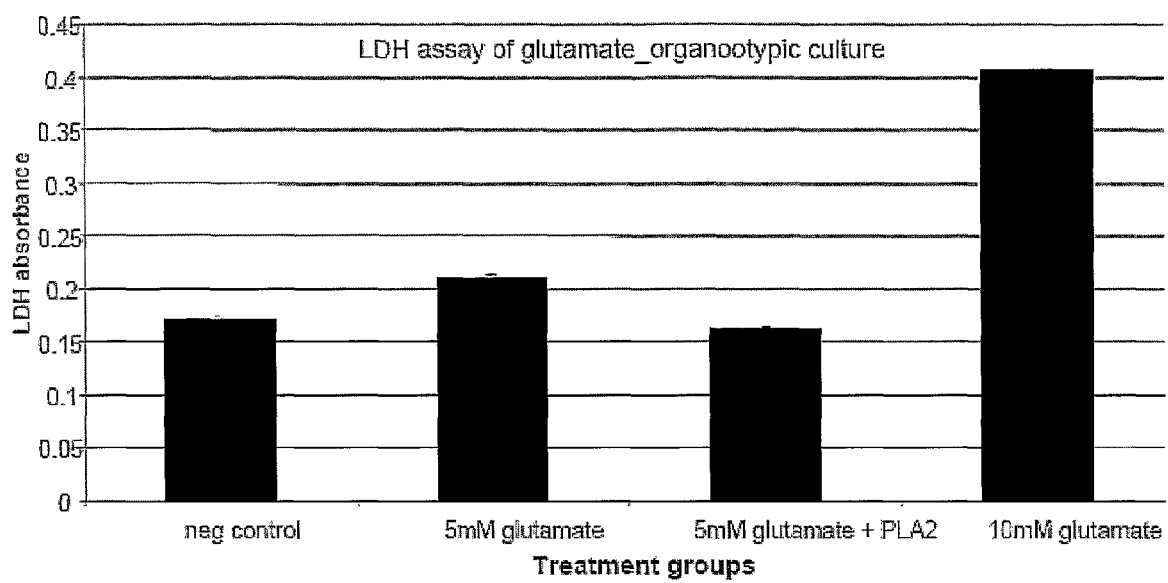

Organotypic hippocampal slices subjected to glutamate (5 mM) insult for 3 hours were treated with NsPLA$_2$ (0.5 ug, 1.0 ug and 2.0 ug) in two time frames, concurrently (during the insult) as well as post-treatment (during recovery). FIG. 10 (A and B) shows the propidium iodide (PI) uptake of the hippocampal slice culture. In both conditions, NsPLA$_2$ appears to render protection at the CA1 and the CA2/3 region. However, more pronounced protection is seen in the CA2/3 region (40% to 60%). The neuroprotection in glutamate induced neuronal injury has been found to be dependent on the concentration of NsPLA$_2$ and higher than that produced by the positive control, NMDA (N-methyl-D-aspartate) antagonist, MK801 (dizocilpine). The LDH (lactate dehydrogenase) assay also showed reduced cytotoxicity upon treatment with NsPLA$_2$ compared to the untreated control with glutamate insult. The percentage of LDH activity is similar to the LDH activity in the normoxic cultures (FIG. 10C).

Figure 11:
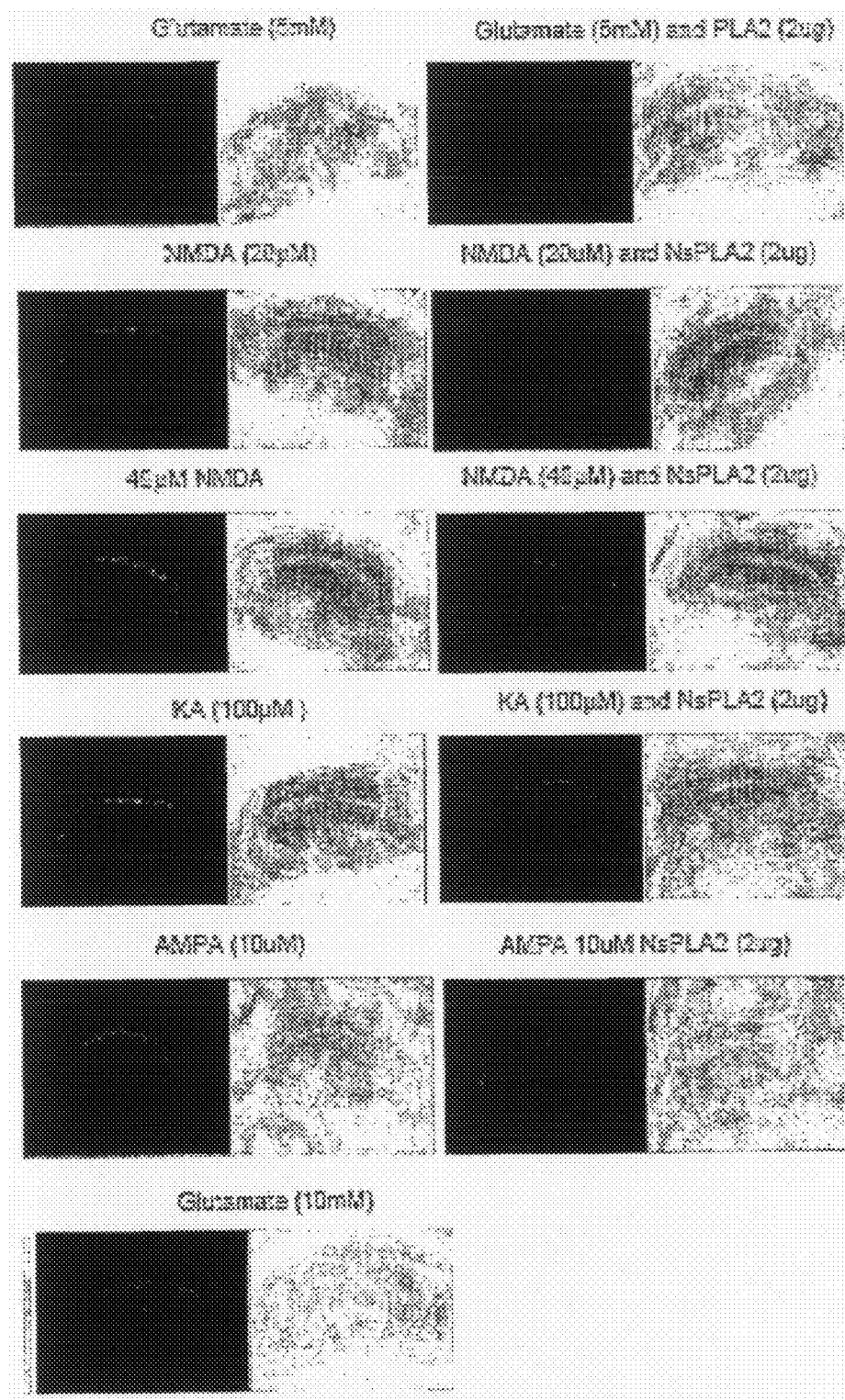

In order to identify the NsPLA$_2$ mediated neuroprotection in the glutamate ediated neuronal injury, we used the specific glutamate receptor (ionotropic) ligand, NMDA (N-methyl-D-aspartate), AMPA (alpha-amino-3-hydroxy-5-methyl-4 isoxazolepropionic acid) and KA (kainic acid) to induce the insult. The concentration of ligands (20 uM NMDA, 100 uM KA and 10 uM AMPA) used was based on 50% PI uptake as reported by Kristensten et al (2001). The cultures were incubated in the absence and presence of NsPLA$_2$ (2 ug/ml) concurrently, for 3 hr. Exposure to 100 uM KA, resulted in severe damage to the CA3 pyramidal cell layer, while 20 uM NMDA and 10 uM AMPA induced significantly higher damage to the CA1 region of the hippocampal slices. Interestingly, addition of NsPLA$_2$ during the insult protected the more vulnerable regions respectively. In NMDA and AMPA mediated neuronal injury, the CA1 region is being protected (70% and 30% respectively). In neuronal injury mediated by KA, 50% neuroprotection is observed at the CA3 region (FIG. 11).

Example 9

Figure 12A:
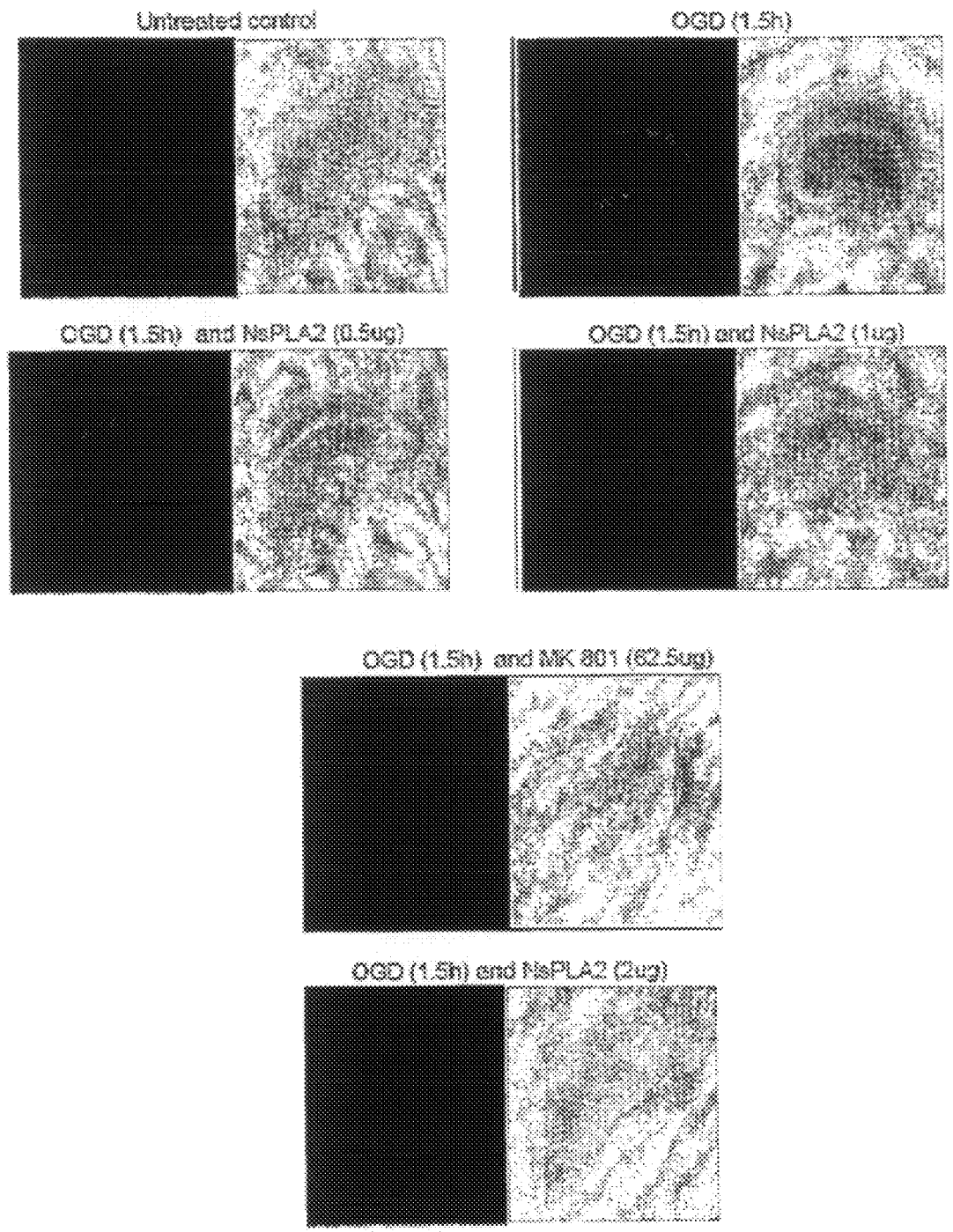
Figure 12B:
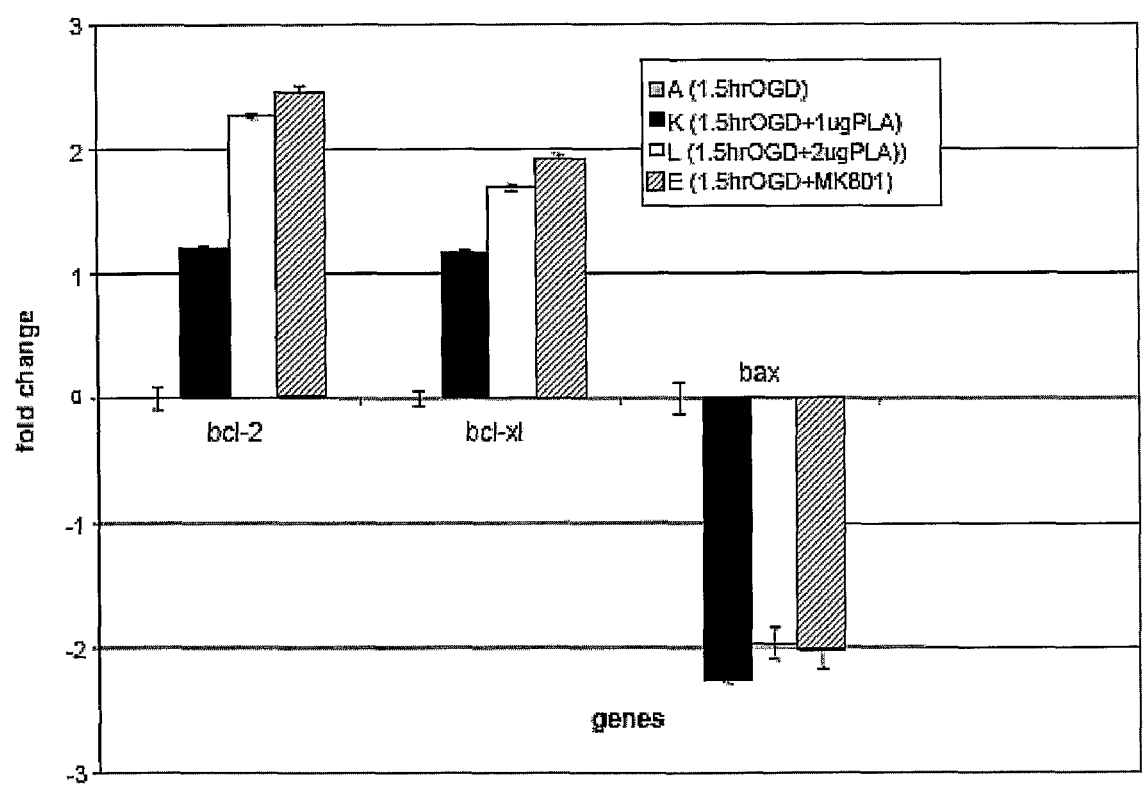

Neuroprotection in Oxygen-Glucose Deprived (OGD) Organotypic Hippocampal Slice Culture In vivo cerebral ischemia is known to be best mimicked in vitro by the oxygen-glucose deprived (OGD) conditions, a well studied model of necrosis. Thus, we carried out experiments using the organotypic hippocampal cultures, in conditions where oxygen is eliminated by using the 95% N$_2$ and 5% CO$_2$ and glucose was deprived in cultures by using culture media without glucose. Addition of NsPLA$_2$ during the insult period (90 mins) rendered neuroprotection to the hippocampal slices (FIG. 12A), in a dose dependant manner. The result showed that NsPLA$_2$ at 2 ug/ml was most effective for neuroprotection, with 95% protection and similar to the MK801 (NMDA antagonist, positive control). In all cases, the NsPLA$_2$ mediated protection is seen in the exclusively in the CA2/3 region of the hippocampal slices. The NMDA antagonist, MK801, which showed protection of neuronal injury upon OGD (oxygen-glucose deprivation) was used as positive control. Real-time gene expression studies (FIG. 12B) showed that the genes encoding anti-apoptotic markers Bcl-2 and Bcl-XL were both up-regulated and the pro-apoptotic marker Bax gene was down-regulated.

REFERENCES

Argraves, W. S., Greene, L. M., Cooley, M. A. and Gallagher, W. M. (2003) *EMBO reports*. 4(12), 1127-1131.

Armugam A, Earnest L, Chung M C, Gopalakrishnakone P, Tan C H, Tan N H, Jeyaseelan K. Cloning and characterization of cDNAs encoding three isoforms of phospholipase A2 in Malayan spitting cobra (*Naja naja sputatrix*) venom. *Toxicon.* 1997 January; 35(1):27-37

Baker-LePain, J. C., Sarzotti, M. and Nicchitta, C. V. (2004. *J. Immunol.* 172(7), 4195-4203.

Barone, F. C., Arvin, B., White, R. F, Miller, A., Webb, C. L., Willette, R. N., Lysko, P. G. and Feuerstein, G. Z. (1997) *Stroke.* 28, 1233-1244.

Bertorelli, R., Adami, M., Di Santo, E. and Ghezzi, P. (1998) *Neurosci. Lett.* 246, 41-44.

Beschomer, R., Engel, S., Mittelbronn, M., Adjodah, D., Dietz, K., Schluesener, H. J. and Meyermann, R. (2000). *Acta Neuropathol.* 100, 627-634.

Blake, G. J. and Ridker, P. M. (2001) *Circ. Res.* 89(9), 763-771.

Bonventre J. V., Huang Z., Reza Taheri M., O'Leary E., Li E., Moskovitz M. A. et al. (1997) Reduced fertility and postischaemic brain injury in mice deficient in cytosolic phospholipase A2. Nature 390: 622625

Buchan, A. M., Slivka, A. and Dong, X. (1992) *Brain Res.* 574, 171-177.

Chen, Z. L. and Strickland, S. (1997) *Cell.* 91, 917-925.

Choi, D. (2000) Stroke. *Neurobiol. Dis.* 7, 552-558.

Del Zoppo, G. J., Schmid-Schonbein, G. W., Mori, E., Copeland, B. R. and Chang, C. M. (1991). *Stroke.* 22, 1276-1283.

Dimagl, U., Iadecola, C. and Moskowitz, M. A. (1999) *Trends Neurosci.* 22, 391-97.

Ellison, J. A., Velier, J. J., Spera, P., Jonak, Z. L., Wang, X., Barone, F. C. and Feuerstein, G. Z. (1998) *Stroke.* 1698-1707.

Ellison, J. A., Velier, J. J., Spera, P., Jonak, Z. L., Wang, X., Barone, F. C. and Feuerstein, G. Z. (1998) *Stroke.* 1698-1707.

Fisher, M. (2004) *Cerebrovasc. Dis.* 17(Suppl 1), 1-6.

Fisher, M. and Schaebitz, W. (2000) *Arch. Intern. Med.* 160, 3196-3200.

Fujimura, M., Gasche, Y., Morita-Fujimura, Y., Massengale, J., Kawase, M. and Chan, P. H. (1999) *Brain Res.* 842, 92-100.

Furlan, A., Higashida, R., Wechsler, L. A., Gent, M., Rowley, H., Kase, C., Pessin, M., Ahuja, A., Callahan, F., Clark, W. M., Silver, F. and Rivera, F. (1999). *JAMA.* 282, 2003-2011.

Furukawa, K., Fu, W., Li, Y., Witke, W., Kwiatkowski, D. J. and Mattson, M. P. (1997) *J. Neurosci.* 17, 8178-8186.

Hakim, A. M. (1987) *J. Neurol. Sci.* 14, 557-559.

Hamann, G. F., Okada, Y., Fitridge, R. and del Zoppo, G. J. (1995) *Stroke.* 26, 2120-2126.

Hsu, C. Y., An, G., Liu, J. S., Xue, J. J., He, Y. Y. and Lin, T. N. (1993) *Stroke.* 24, 178-181.

Hunter, J., Green, A. R. and Cross, A. J. (1995) *Trends in Pharmacol. Sci.* 16, 123-128.

Iadecola, C. (1997). *Trends Neurosci.* 20, 132-139.

Izeboud, C. A., Hoebe, K. H., Grootendorst, A. F., Nijmeijer, S. M., van Miert, A. S., Witkamp, R. R. and Rodenburg, R. J. (2004). *Inflamm Res.* 53(3), 93-9

Jeyaseelan K, Armugam A, Donghui M, Tan N H. Structure and phylogeny of the venom group I phospholipase A (2) gene. *Mol Biol Evol.* 2000 July; 17(7):1010-21

Karpiak, S. E., Tagliavia, A. and Wakade, C. G. (1989) *Annu. Rev. Pharmacol. Toxicol.* 29, 403-414.

Kilic, E., Bahr, M. and Hermann, D. M. (2001) *Stroke.* 32, 2641-2647.

Kini R. M. (1997) Phospholipase A2—a complex multifunctional protein puzzle. In: Venom Phospholipase A2 Enzymes: Structure, Function and Mechanism, pp. 1-28, Kini R. M. (ed.), Wiley, Chichester Kinouchi, H., Epstein, C. J., Mizuki, T., Carlson, E., Chen, S, F. and Chan, P. H. (1991). *Proc. Natl. Acad. Sci. USA.* 88, 11158-11162

Kondo, T., Reaume, A. G., Huang, T. T., Carlson, E., Murakami, K., Chen, S. F., Hoffman, E. K., Scott, R. W., Epstein, C. J. and Chan, P. H (1997) *J. Neurosci.* 17, 4180-4189.

Li, J., Brown, L. F., Laham, R. J., Volk, R. and Simons, M. (1997) *Circ. Res.* 81, 785-796.

Liu, T., Clark, R. F., McDonnell, P. C., Young, P. R., White, R. F., Barone, F. C. and Feuerstein, G. Z. (1994). *Stroke.* 25, 1481-1488.

Liu, T., McDonnell, P. C., Young, P. R., White, R. F., Siren, A. L., Barone, F. C. and Feuerstein, G. Z. (1993) *J. Cereb. Blood Flow Metab.* 15, 166-171.

MacManus, J. P., Graber, T., Luebbert, C., Preston, E., Rasquinha, I., Smith, B. and Webster, J. (2004 *J. Cereb. Blood Flow. Metab.* 24, 657-667

Matsui, T., Mori, T., Tateishi, N., Kagamiishi, Y., Satoh, S., Katsube, N., Morikawa, E., Morimoto, T., Ikuta, F. and Asano, T. (2002). *J. Cereb. Blood Flow Metab.* 22, 711-722.

McKay, S., Bromhaar, M. M., de Jongste, J. C., Hoogsteden, H. C., Saxena, P. R. and Sharma, H. S. (2001) *Mediators Inflamm.* 10(3), 135-42.

Nagahiro, S., Uno, M., Sato, K., Goto, S., Morioka, M. and Ushio, Y. (1998). *J. Med. Invest.* 45, 57-70.

Nagai, N., Yamamoto, S., Tsuboi, T., Ihara, H., Urano, T., Takada, Y., Terakawa, S, and Takada, A. (2001) *J. Cereb. Blood Flow Metab.* 21, 631-634.

Nowak, T. S., Ikeda, J. J. and Nakajima, T. (1990) *Stroke.* 21(Suppl 111), 107-111.

Ombregt et al., A System of Orthopaedic Medicines, Elsevier Health Sciences, 2003, page 39

Paglini, G., Kunda, P., Quiroga, S., Kosik, S, and Caceres, A. (1998) *J. Cell Biol.* 143, 443-455.

Pisani, A., Bonsi, P. and Calabresi, P. (2004) *Cell Calcium.* 36, 277-284.

Read, S. J., Parsons, A. A., Harrison, D. C., Philpott, K., Kabnick, K., O'Brien, S., Clark, S., Brawner, M., Bates, S., Gloger, I., Legos, J. J. and Barone, F. C. (2001). *J. Cereb. Blood Flow Metab.* 21, 755-778.

Rosenberg, G. A. (1995) *J. Neurotrauma.* 12, 833-842.

Rosenberg, G. A., Navratil, M., Barone, F. C., Feuerstein, G. Z. (1996) *J. Cereb. Blood Flow Metab.* 16, 360-366.

Rothwell, N. J. and Hopkins, S. J. (1995). *Trends Neurosci.* 18, 130-136.

Schaller, B. and Graf, R. (2004) *J. Cereb. Blood Flow. Metab.* 24, 351-371.

Sherman, D. G., Atkinson, R. P., Chippendale, T., Levin, K. A., Ng, K., Futrell, N., Hsu, C. Y. and Levy, D. E. (2000) *JAMA.* 283, 2395-2403.

Sim, F. J., Zhao, C., Li, W. W., Lakatos, A. and Franklin, J. M. (2002) *Mol. Cell. Neurosci.* 20, 669-682.

Smith, W. S. (2004) *J. Vasc. Interv. Radiol.* 15, S3-12.

Tan N H, Arunmozhiarasi A. The anticoagulant activity of Malayan cobra (*Naja naja sputatrix*) venom and venom phospholipase A2 enzymes. *Biochem Int.* 1989 October; 19(4):803-10.

Tsirka, S. E., Rogove, A. D., Bugge, T. H., Degen, J. L. and Strickland, S. (1997). *J. Neurosci.* 17, 543-552

Uemura, Y., Kowall, N. W. and Moskowitz, M. A. (1991) *Brain Res.* 552, 99-105.

Valentin et al. Biochimicha et Biophysica Acta 1488 (2000) 59-70.

Walther, T., Olah, L., Harms, C., Maul, B., Bader, M., Hortnagl, H., Schultheiss, H. P. and Mies, G. (2002). *FASEB J.* 16, 169-176.

Wang, H., Zhan, Y., Xu, L., Feuerstein, G. Z. and Wang, X. (2001). *Stroke.* 32(4), 1020-1027.

Wang, X. K., Louden, C., Yue, T. L., Ellison, J. A., Barone, F. C., Solleveld, H. A. and Feuerstein, G. Z. (1998a) *J. Neurosci.* 18(6), 2075-2083.

Wang, X. K., Xu, L., Wang, H., Zhan, Y. T., Pure, E. and Feuerstein, G. Z. (2002). *J. Neurochem.* 83, 1172-1179.

Wang, X. K., Yue, T. L., Barone, F. C. and Feuerstein, G. Z. (1995b). *Stroke.* 26, 661-666.

Wang, X. K., Yue, T. L., Young, P. R., Barone, F. C. and Feuerstein, G. Z. (1995a) *J. Cereb. Blood Flow Metab.* 15, 166-171.

Warlow, C P., Dennis, M S., van Gijn, J et al (2001) In *Stroke: practical guide to management.* Oxford: Blackwell Science, 223-300

Warlow, C P., Sudlow, C., Dennis, M S., Wardlaw, J and Sandercock, P (2003) *Lancet* 362: 1211-24

Weisbrot-Lefkowitz, M., Reuhl, K., Perry, B., Chan, P. H., Inouye, M. and Mirochnitchenko, O. (1998) *Mol. Brain. Res.* 53, 333-338.

Yang, G., Chan, P. H., Chen, S. F., Babuna, O. A., Simon, R. P. and Weinstein, P. R. (1994) *Neurosurgery.* 34(2), 339-345.

Ye, Z. R., Liu, K. F. and Garcia, J. H. (2001) In: Current Review of Cerebrovascular Disease. Fisher, M. and Bogousslavsky, J. (ed). *Current Medicine, Philadelphia.* pp 15 24.

Zhao, Q. et al (1994) *Acta Physiol. Scand.* 152, 349-350.

Zivin, J. A., Fisher, M., DeGirolami, U., Hemenway, C. C. and Stashak, J. A. (1985) *Science.* 230, 1289-1292.

Zivin, J. A., Lyden, P. D., DeGirolami, U., Kochhar, A., Mazzarella, V., Hemenway, C. C. and Johnston, P. (1988) *Arch. Neurol.* 45, 387-391.

---

The invention claimed is:

1. A method for the treatment of ischemia comprising administering to a subject a therapeutically effective amount of at least one phospholipase $A_2$ having an amino acid sequence comprising the sequence of SEQ ID NO:2, and wherein optionally, the at least one phospholipase $A_2$ having an amino acid sequence comprising the sequence of SEQ ID NO:2 is administered in conjunction with at least one pharmaceutically acceptable, excipient, diluent, carrier, or adjuvant.

2. The method according to claim 1, wherein the at least one phospholipase $A_2$ having an amino acid sequence comprising the sequence of SEQ ID NO:2 is a secretory or a cytoplasmic phospholipase.

3. The method according to claim 2, wherein the secretory phospholipase is pancreatic, synovial, venomous phospholipase, or combination thereof.

4. The method according to claim 1, wherein the phospholipase is a neutral venom phospholipase.

5. The method according to claim 1, wherein the phospholipase $A_2$ having an amino acid sequence comprising the sequence of SEQ ID NO:2 is selected from any one of Group I to Group XI phospholipase $A_2$.

6. The method according to claim 1, wherein the phospholipase $A_2$ having an amino acid sequence comprising the sequence of SEQ ID NO:2 is from snake venom.

7. The method according to claim 1, wherein the phospholipase $A_2$ having an amino acid sequence comprising the sequence of SEQ ID NO:2 is from *Naja sputatrix* venom.

8. The method according to claim 1, wherein the ischemia is selected from the group consisting of cerebral ischemia, cardiac ischemia, skeletal muscle ischemia and transient focal ischemia.

9. The method according to claim 1, wherein the treatment comprises inducing neuroprotective effects in a subject at risk of ischemic stroke.

10. The method according to claim 1, wherein the phospholipase $A_2$ having an amino acid sequence comprising the sequence of SEQ ID NO:2reduces (a) ischemic infarct size compared to tissue plasminogen activator (tPA) or N-methyl-D-aspartate antagonist (NMDA) dizocilpine maleate (MK801); or (b) ischemic cell death compared to tPA or MK801.

11. The method according to claim 1, wherein administration of phospholipase $A_2$ having an amino acid sequence comprising the sequence of SEQ ID NO:2up-regulates at least one anti-apoptotic gene or gene transcript.

12. The method according to claim 11, wherein the anti-apoptotic gene comprises Bcl-2 and/or Bcl-XL.

13. The method according to claim 1, wherein administration of phospholipase $A_2$ having an amino acid sequence comprising the sequence of SEQ ID NO:2 down-regulates at least one pro-apoptotic gene or gene transcript.

14. The method according to claim 13, wherein the pro-apoptotic gene comprises Bax.

15. The method according to claim 1, wherein the treatment comprises administering the phospholipase $A_2$ having an amino acid sequence comprising the sequence of SEQ ID NO:2:

at least once or continuously, before the onset of the ischemia;

at least once or continuously, during the onset of the ischemia; or at least once or continuously, after the onset of the ischemia.

16. The method according to claim 1, wherein the phospholipase $A_2$ having an amino acid sequence comprising the sequence of SEQ ID NO:2 is administered at least once or continuously during or until 15 minutes after the onset of the ischemia.

* * * * *